US008695996B2

(12) United States Patent
Janick et al.

(10) Patent No.: US 8,695,996 B2
(45) Date of Patent: Apr. 15, 2014

(54) MEDICAL EMERGENCY CRASH CART

(75) Inventors: James J. Janick, Hanover Township, PA (US); Robert J. Welch, Rochester, NY (US); Robert R. Steele, Sweet Valley, PA (US); Sanjeeb Sinha, Maharastra (IN)

(73) Assignee: Metro Industries Inc., Reno, NV (US)

( * ) Notice: Subject to any disclaimer, the term of this patent is extended or adjusted under 35 U.S.C. 154(b) by 579 days.

(21) Appl. No.: 12/997,554

(22) PCT Filed: May 26, 2009

(86) PCT No.: PCT/US2009/045153
§ 371 (c)(1),
(2), (4) Date: Jan. 11, 2011

(87) PCT Pub. No.: WO2009/151944
PCT Pub. Date: Dec. 17, 2009

(65) Prior Publication Data
US 2012/0007323 A1    Jan. 12, 2012

(30) Foreign Application Priority Data

Jun. 13, 2008   (IN) .......................... 1253/MUM/2008

(51) Int. Cl.
*B62B 5/04*    (2006.01)
*B62B 3/00*    (2006.01)
(52) U.S. Cl.
USPC ...................................... 280/79.3; 280/47.35

(58) Field of Classification Search
USPC .................... 280/79.11, 79.3, 47.131, 47.34; 312/218, 219, 305, 351.13
See application file for complete search history.

(56) References Cited

U.S. PATENT DOCUMENTS

| 4,276,962 | A | * | 7/1981 | Aulik | 188/1.12 |
| 4,790,610 | A | | 12/1988 | Welch et al. | 312/218 |
| 4,875,696 | A | | 10/1989 | Welch et al. | 280/47.34 |
| 5,290,058 | A | * | 3/1994 | Adams et al. | 280/651 |
| 5,673,983 | A | | 10/1997 | Carlson et al. | 312/218 |
| 6,158,830 | A | | 12/2000 | Johnson et al. | 312/218 |
| 6,378,963 | B1 | | 4/2002 | Relyea et al. | 312/218 |
| 6,609,719 | B2 | | 8/2003 | Heien | 280/5.26 |
| 6,725,956 | B1 | | 4/2004 | Lemire | 180/15 |
| 7,044,569 | B1 | * | 5/2006 | Relyea et al. | 312/249.11 |
| 7,370,867 | B2 | | 5/2008 | Olson et al. | 280/79.11 |

* cited by examiner

*Primary Examiner* — J. Allen Shriver, II
*Assistant Examiner* — Bridget Avery
(74) *Attorney, Agent, or Firm* — Fitzpatrick, Cella, Harper & Scinto

(57) ABSTRACT

A utility cart includes an auxiliary swivel caster wheel assembly, a locking mechanism, and a trigger mechanism for causing the locking mechanism to releasably lock the auxiliary swivel caster wheel assembly. The auxiliary swivel caster wheel assembly is unlocked to enable the auxiliary swivel caster wheel to rotate about a vertical axis for improved maneuverability in small areas, and is locked to hold the auxiliary swivel caster wheel in a predetermined position for improved steering as the cart is moved from one location to another. The trigger mechanism is disposed on a steering handle to enable dynamic actuation of the locking mechanism while the cart is in motion.

19 Claims, 21 Drawing Sheets

MEDICAL EMERGENCY CRASH CART

BACKGROUND OF THE INVENTION

1. Field of the Invention

The present invention relates to an auxiliary swivel caster wheel assembly and a caster direction-locking mechanism for a mobile utility cart, and more particularly to such a wheel assembly and locking mechanism for a mobile utility cart commonly called a "medical emergency crash cart" or simply a "crash cart", for medical emergency use in hospitals and other medical institutions. The auxiliary swivel caster wheel assembly and direction-locking caster mechanism in accordance with the present invention provide the crash cart with improved high speed stability and maneuverability. A trigger mechanism for selectively locking and unlocking the direction-locking caster mechanism also is included.

2. Description of Related Art

A medical emergency crash cart commonly contains medical equipment, instruments, and supplies that may be required while responding to medical emergencies, particularly for medical procedures practiced in cases of cardiac emergencies. However, the crash cart may be equipped for any type of medical emergency. The crash cart generally includes a housing having a plurality of drawers, shelves, and/or compartments for storing medical equipment and supplies such as syringes and drugs. The housing is supported by a plurality of wheels or casters so that it may be moved rapidly from its place of storage to a location of a medical emergency. To provide maximum efficiency during a medical emergency, a crash cart must therefore provide both agile and stable mobility.

One drawback of many known crash carts is a lack of stability during high speed travel. First, as a crash cart must be able to maneuver quickly in small areas of patients' or hospital emergency rooms, it is desirable to support the housing on swivel casters. Second, as medical equipment, instruments, and supplies are expensive, hospitals may maintain only a limited number of crash carts (e.g. one crash cart per floor or station). Therefore, when a medical emergency occurs, a crash cart operator must rush the cart through the hospital corridors often over relatively long distances to a patient. However, the swivel casters may cause the cart to be difficult to steer at high speeds particularly when an attempt is made to change the direction of movement, for example, by going around corners in corridors or turning into a patient's room. Therefore, the crash cart operator must either reduce his speed through the corridors or risk overturning the cart. The risk of overturning increases when the operator must negotiate the cart around a corner, as swivel casters do not provide a firm pivot about which to turn but rather permit inertia of the cart to cause it to tend to continue to move in its original direction. Alternatively, a crash cart may be operated by two persons. However, this is less efficient and may, in fact, not be possible during a given emergency.

U.S. Pat. No. 4,790,610 (Welch et al.), U.S. Pat. No. 4,875,696 (Welch et al.), and U.S. Pat. No. 7,370,867 (Olson et al.) disclose mechanisms for selectively locking swivel caster wheel assemblies in predetermined positions. However, while the mechanisms disclosed in these patents have many advantages, they are not well suited for dynamic actuation while a cart is in motion. For example, actuators for these mechanisms may be located on a side of a cart and/or may be positioned for actuation by an operator's foot, or may be otherwise inconvenient for the operator to actuate while the cart is in motion.

In addition, U.S. Pat. No. 6,725,956 (Lemire) discloses a hospital bed having four wheels in contact with a floor surface, and a motorized assembly that is employed to raise and lower an auxiliary or fifth wheel away from and toward the floor. When the fifth wheel is raised, the hospital bed functions as a conventional hospital bed. When the fifth wheel is lowered, it contacts the floor surface and the motorized assembly causes the fifth wheel to rotate, which propels the hospital bed. The fifth wheel is held at a predetermined position relative to a frame of the hospital bed, thus, the fifth wheel must be raised when maneuvering the hospital bed in a small area, such as a patient's room. However, the fifth wheel cannot be raised and lowered quickly. Accordingly, the fifth wheel disclosed in the Levine Patent is not well-suited for use in emergency situations.

For these and other reasons, the crash carts and related mechanisms for improving mobility of wheeled apparatuses of the prior art are not entirely satisfactory. A need exists for an improved crash cart and related mechanisms for providing even greater high speed stability and maneuverability.

SUMMARY OF THE INVENTION

Generally speaking, the present invention will be referred to as a "cart," which is highly maneuverable and which may incorporate an enclosed cabinet for storing items, such as medical supplies used in responding to medical emergencies. However, the present invention may be used in conjunction with a variety of wheeled apparatus, including stretchers, medical storage carts, and hospital beds, for example, as well as other utility carts that have general application outside of the medical field. Accordingly, the present invention is not limited to crash or other medical carts, but may be used in conjunction with any wheeled structure that can benefit from improved maneuverability and stability.

In one embodiment, the present invention is directed to a cart having a first end and a second end. The cart includes at least four swivel casters supporting the cart. A first two of the swivel casters are adjacent each other and support the cart in the region of the first end, and a second two of the swivel casters are adjacent each other and support the cart in the region of the second end. Each swivel caster includes a wheel rotatable about a horizontal axis, and is mounted with the cart for swiveling movement about a generally vertical axis. An auxiliary swivel caster assembly also supports the cart. The auxiliary swivel caster assembly includes a wheel rotatable about a horizontal axis, and is mounted with said cart for swiveling movement about a generally vertical axis. The cart also includes locking means selectably operable to lock the auxiliary swivel caster assembly against swiveling movement when the wheel of the auxiliary swivel caster assembly swivels to a predetermined position. Further, the cart includes actuator means for actuating the locking means to selectably engage and disengage the auxiliary swivel caster assembly.

In another embodiment, the present invention is directed to cart including a base portion. A pair of leading end swivel casters support the base portion, each of the pair of leading end swivel casters includes a rotatable wheel. A pair of trailing end swivel casters supporting the base portion, each of the pair of trailing end swivel casters includes a rotatable wheel. An auxiliary swivel caster assembly also supports the base portion, the auxiliary swivel caster assembly swivels about a substantially vertically extending axis, and includes a rotatable wheel. The cart also includes means for urging the wheel of the auxiliary swivel caster assembly toward a floor supporting the cart. A locking mechanism engages the auxiliary swivel caster assembly in a locked position to prevent swivel action thereof, when the auxiliary swivel caster assembly is rotated about its axis to a predetermined position. Further, the cart includes means for biasing the locking mechanism toward an unlocked position to permit swivel action of the auxiliary swivel caster assembly. An actuator is operable when actuated to move the locking mechanism from the unlocked position, and when the actuator is deactivated to permit the locking mechanism to be biased by the biasing means toward the unlocked position. The cart also includes means located on said cart for operating said actuator with a user's hand.

DETAILED DESCRIPTION OF THE INVENTION

Initially, the principal features of the present invention will be described generally in order to provide an overview of its various aspects. Then those features will be described in detail.

Figure 1:
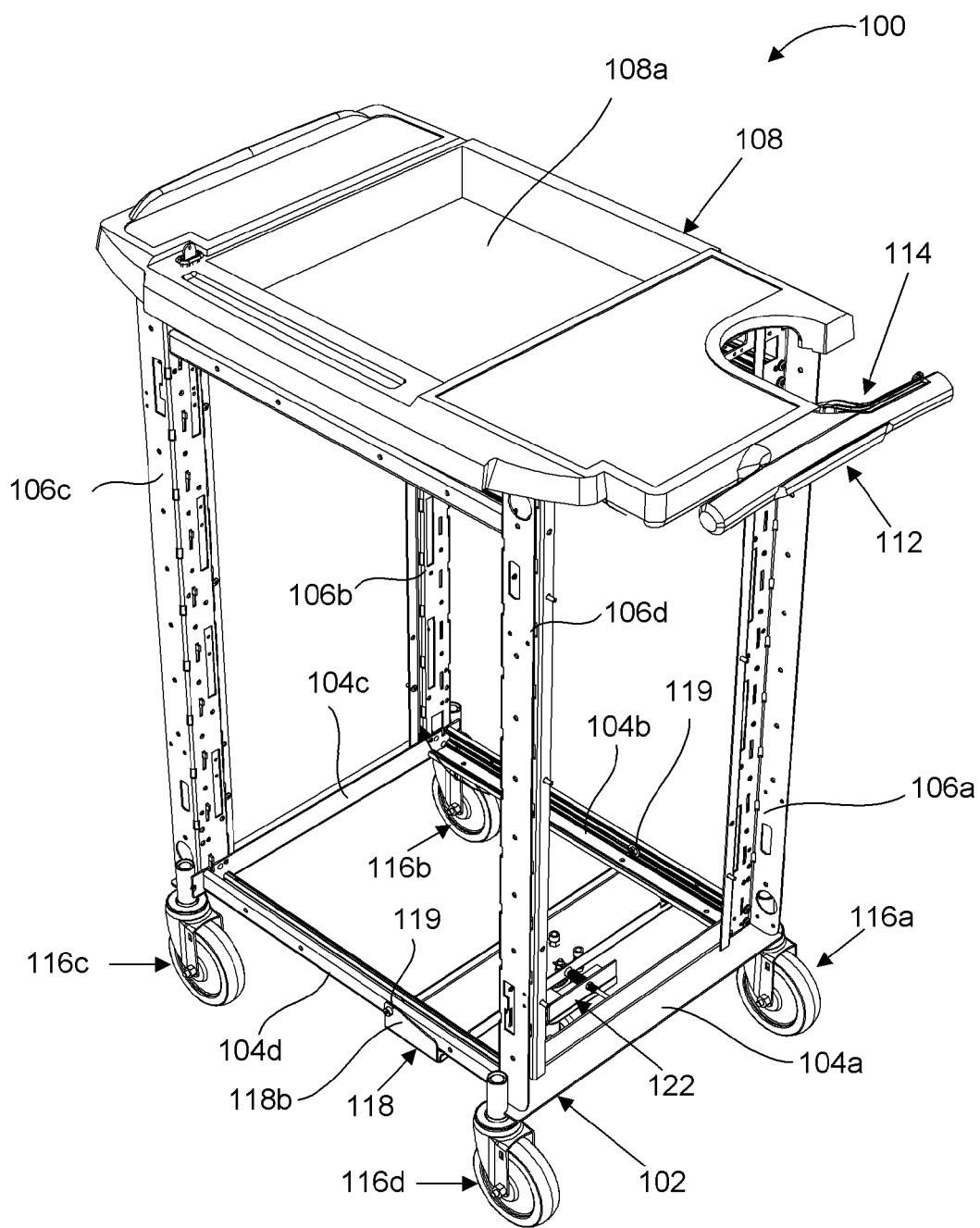
FIG. 1 is a perspective view, taken from the front top right, of a preferred embodiment of a crash cart in accordance with the present invention.
Figure 2:
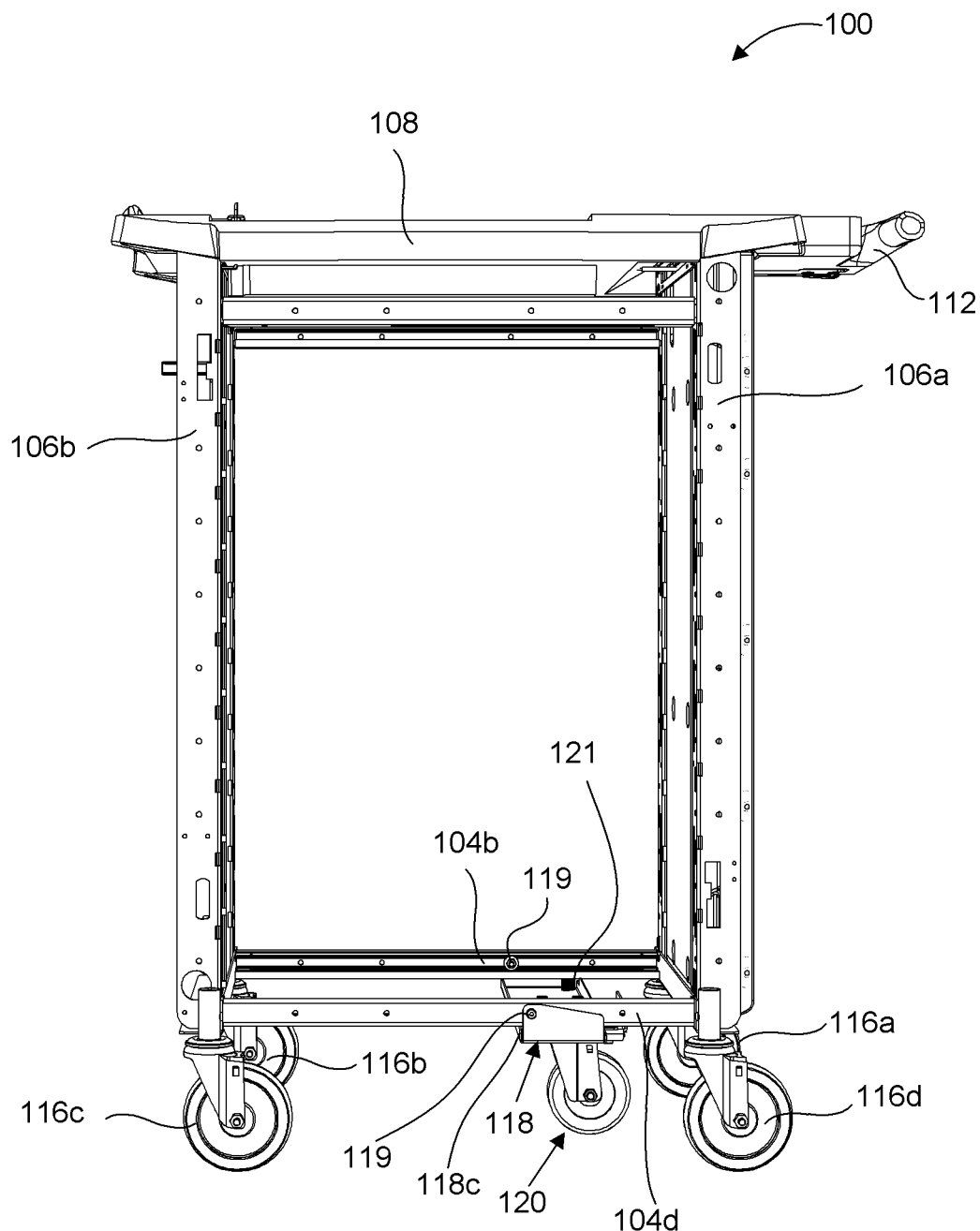
FIG. 2 is a perspective view taken from the front of the crash cart illustrated in FIG. 1.
Figure 3:
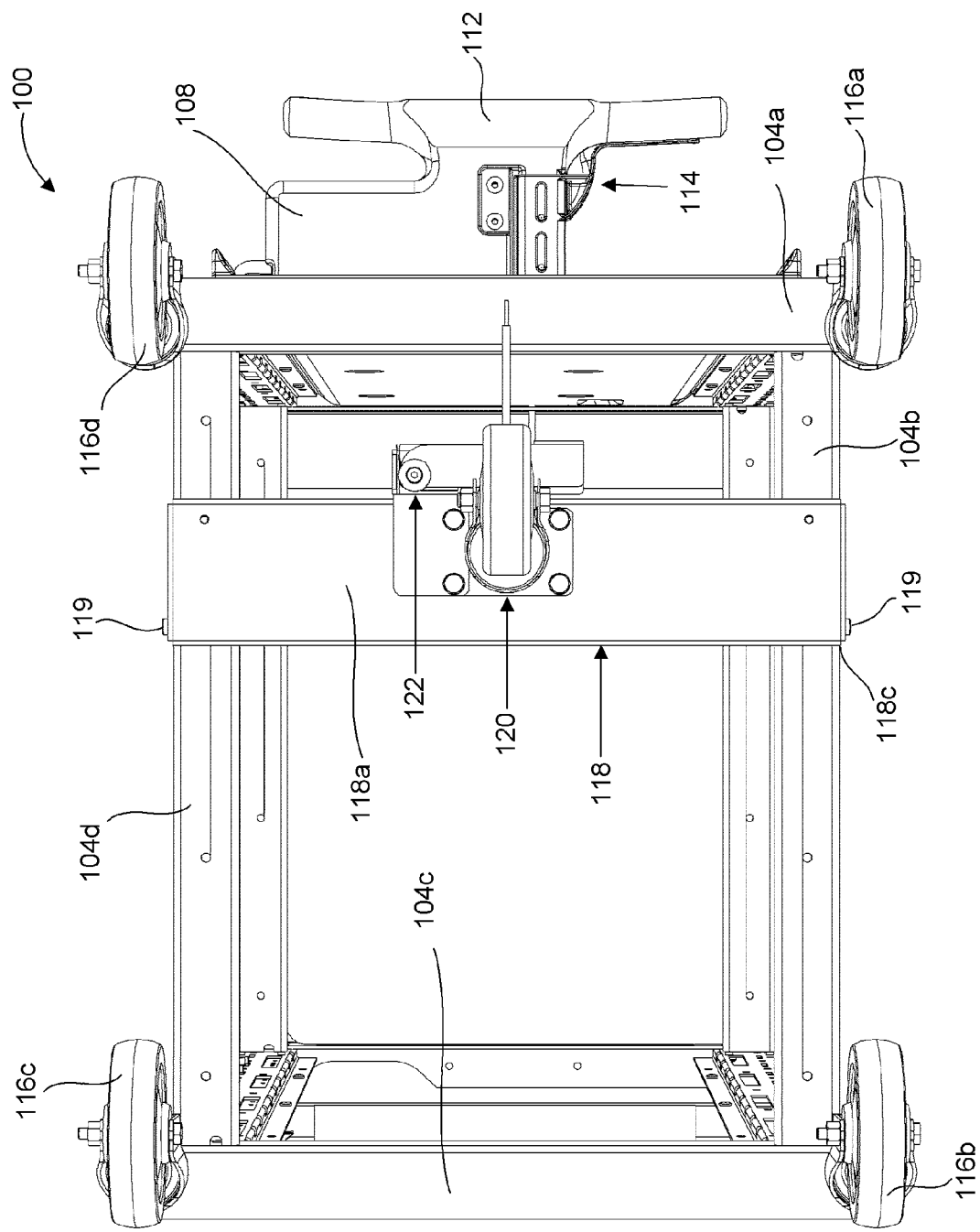
FIG. 3 is a perspective view taken from the bottom of the crash cart illustrated in FIG. 1.

FIGS. 1 through 3 show one embodiment of a crash cart 100 according to the present invention. As shown in those figures, the crash cart 100 has a substantially rectangular horizontal cross-section or foot print as defined by a base portion 102. The base portion 102 is comprised of four horizontal base members 104a, 104b, 104c, and 104d. Four vertical support members 106a, 106b, 106c, and 106d are attached to or near respective corners of the base portion 102. Side panels (not shown) may be attached to the vertical support members 106a, 106b, 106c, and 106d to form an enclosure in which shelves and/or drawers are provided for holding medical supplies. The base portion 102 and vertical support members 106a, 106b, 106c, and 106d could be integrally formed, or constructed according to other known techniques without departing from the scope of the invention.

An upper member 108 is attached to upper ends of the vertical support members 106a, 106b, 106c, and 106d, for example using a plurality of fasteners and screws (not shown). The upper member 108 has a recessed portion 108a for holding medical supplies. In addition, the upper member 108 includes a handle 112 for steering the cart 100. A trigger mechanism 114 is slidably attached to the handle 112, as will be described below. The trigger mechanism 114 preferably is disposed near the handle 112 so that it can be actuated while a cart operator (not shown) is steering the cart 100. In the exemplary embodiment, the upper member 108 and the handle 112 are integrally formed. However, in other embodiments the upper member 108 and the handle 112 are discrete components attached according to known techniques.

Four conventional swivel caster wheel assemblies 116a, 116b, 116c, and 116d are provided at or near respective corners of the base portion 102. In addition, an auxiliary wheel support member 118 is attached to the base portion 102, generally toward the rear end of the cart 100, i.e., the end where the handle 112 is provided. More specifically, the wheel support member 118 is formed with a lower plate 118a, which spans the distance between front and rear base members 104d and 104b, and opposing upstanding flanges 118b each at one extreme end of the lower plate 118a thereby to be outside of the base members 104d and 104b. Each flange 118b is attached to the adjacent base member 104d and 104b by a pivot pin 119 so that a rear edge of the support member can pivot toward and away from a supporting floor.

Auxiliary Swivel Caster Wheel Assembly

First Embodiment

An auxiliary swivel caster wheel assembly 120 is attached to the auxiliary wheel support member 118. The auxiliary swivel caster wheel assembly 120 may be attached to the auxiliary wheel support member 118 in a center portion thereof, i.e., midway between horizontal base members 104b and 104d. Alternatively, the auxiliary swivel caster wheel assembly 120 may be biased or offset from the center portion of the auxiliary wheel support member 118. That is, the auxiliary swivel caster wheel assembly 120 may be attached to the auxiliary wheel support member 118 at a position that is closer to one of the horizontal base members 104b and 104d than to the other of the horizontal base members 104b and 104d.

The auxiliary swivel caster wheel assembly 120 is attached to the auxiliary wheel support member 118 using a plurality of nuts and bolts (not labeled), for example. As will be described in detail below, a caster direction-locking mechanism 122 also is attached to the auxiliary wheel support member 118 to releasably engage the auxiliary swivel caster wheel assembly 120 to permit or prevent rotation of the auxiliary swivel caster wheel assembly 120.

Figure 4:
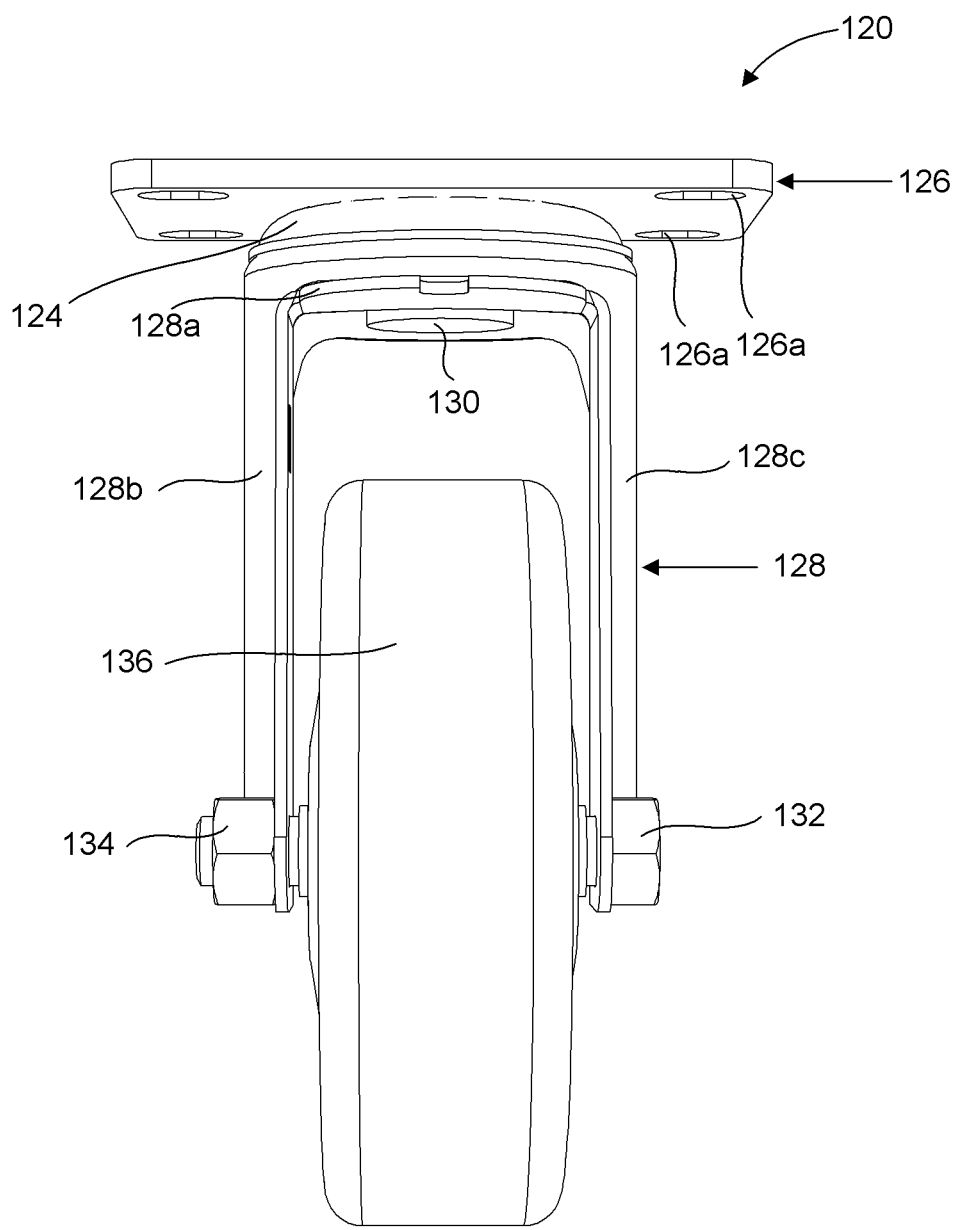
FIG. 4 is a perspective view taken from the front of an auxiliary swivel caster wheel assembly in accordance with an embodiment of the present invention.
Figure 5:
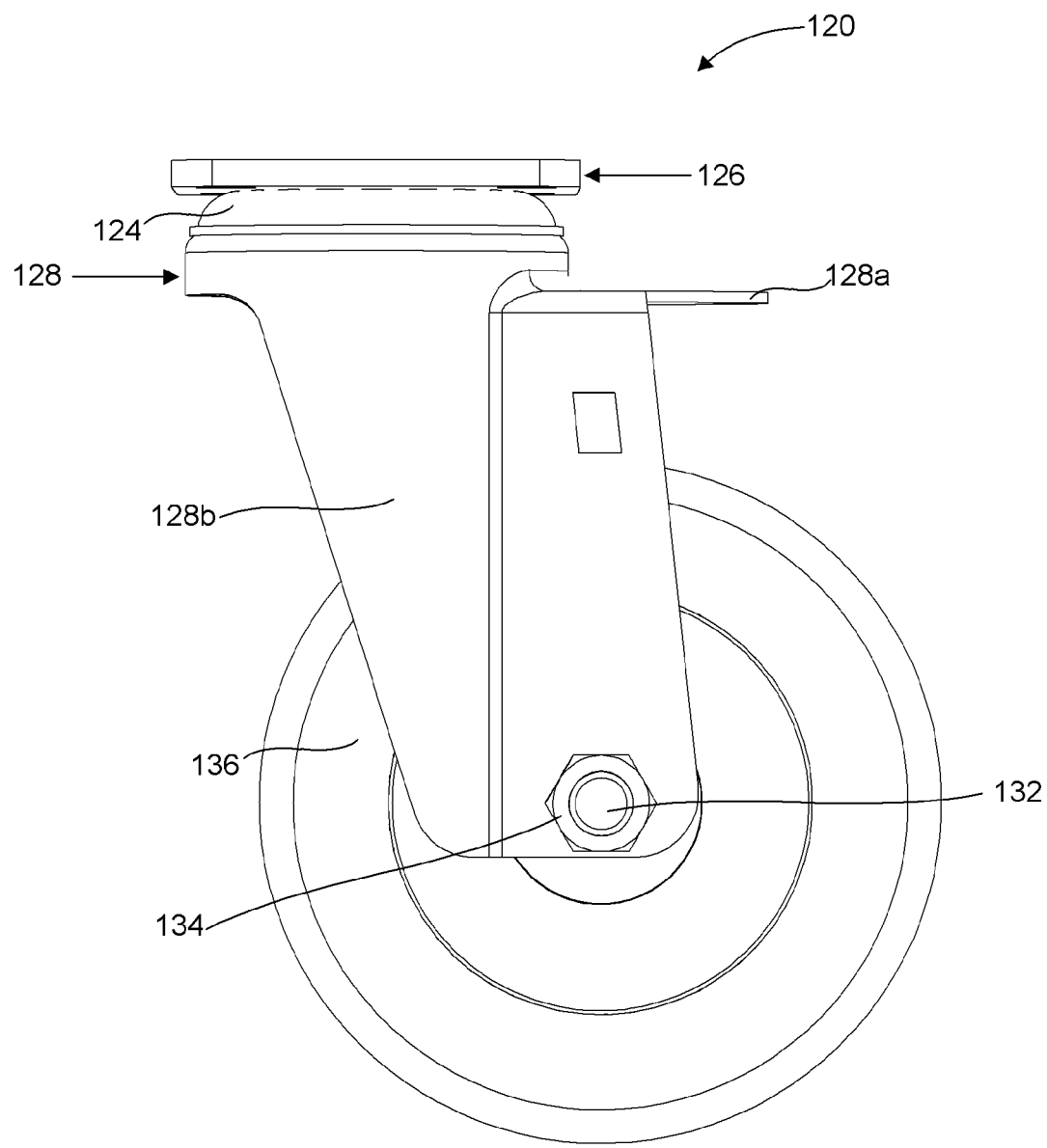
FIG. 5 is a side view of the auxiliary swivel caster wheel assembly illustrated in FIG. 4.

An embodiment of the auxiliary swivel caster wheel assembly 120 of the present invention is described with reference to FIGS. 4 through 6. A swivel mount 124 is rigidly attached to a mounting plate 126, for example, by a welding process. The mounting plate 126 includes a plurality of apertures 126a formed therein, through which a plurality of bolts (not shown in FIGS. 4 through 6) are inserted to secure the auxiliary swivel caster wheel assembly 120 to the auxiliary wheel support member 118.

A generally inverted U-shaped horn 128 is rotatably mounted to the swivel mount 124. More particularly, a post 130 is provided within the swivel mount 124 and bearings (not shown) are disposed about the post 130. The bearings (not shown) enable the horn 128 to rotate or swivel freely about the post 130, with a full 360° of rotational freedom, as is customary with conventional swivel caster wheels. The post 130 serves as a vertical axis of rotation for the horn 128.

The horn 128 includes a top portion 128a, a first leg portion 128b, a second leg portion 128c, and a notch 128d formed in the top portion 128a. An aperture (not shown) is formed in each of the first leg portion 128b and the second leg portion 128c of the horn 128. A threaded end of a bolt 132 is inserted though the aperture of the second leg portion 128c, an aperture (not shown) of a wheel 136, and the aperture of the first leg portion 128b. A nut 134 is secured to the threaded portion of the bolt 132. The bolt 132 serves as a horizontal axis of rotation for the wheel 136. Bearings (not shown) disposed within the wheel 136 enable the wheel 136 to rotate about the bolt 132, with a full 360° of rotational freedom.

As shown in FIG. 2, the wheel support member 118 is urged to rotate in the clockwise direction by a pair of comparison springs 121 each interposed between the top of the lower plate 118a and a bottom surface of one of the base members 104d and 104b. In this way the wheel 136 of the assembly 120 is always urged toward a supporting floor. Rotation of the support member 118 as described is limited by interference of forward edge 118c with the base members 104d and 104b.

Figure 6:
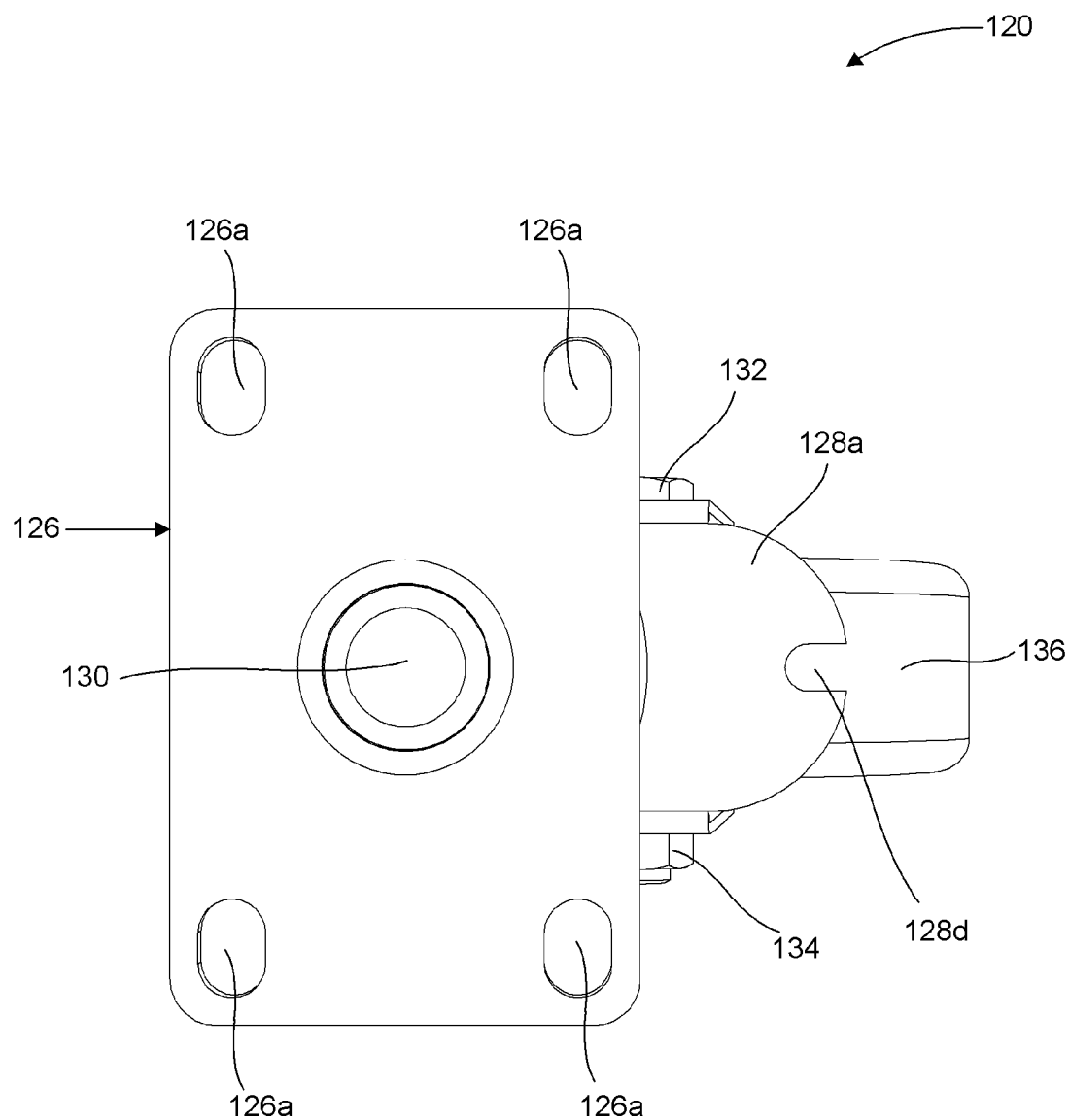
FIG. 6 is a top view of the auxiliary swivel caster wheel assembly illustrated in FIG. 4.
Figure 7:
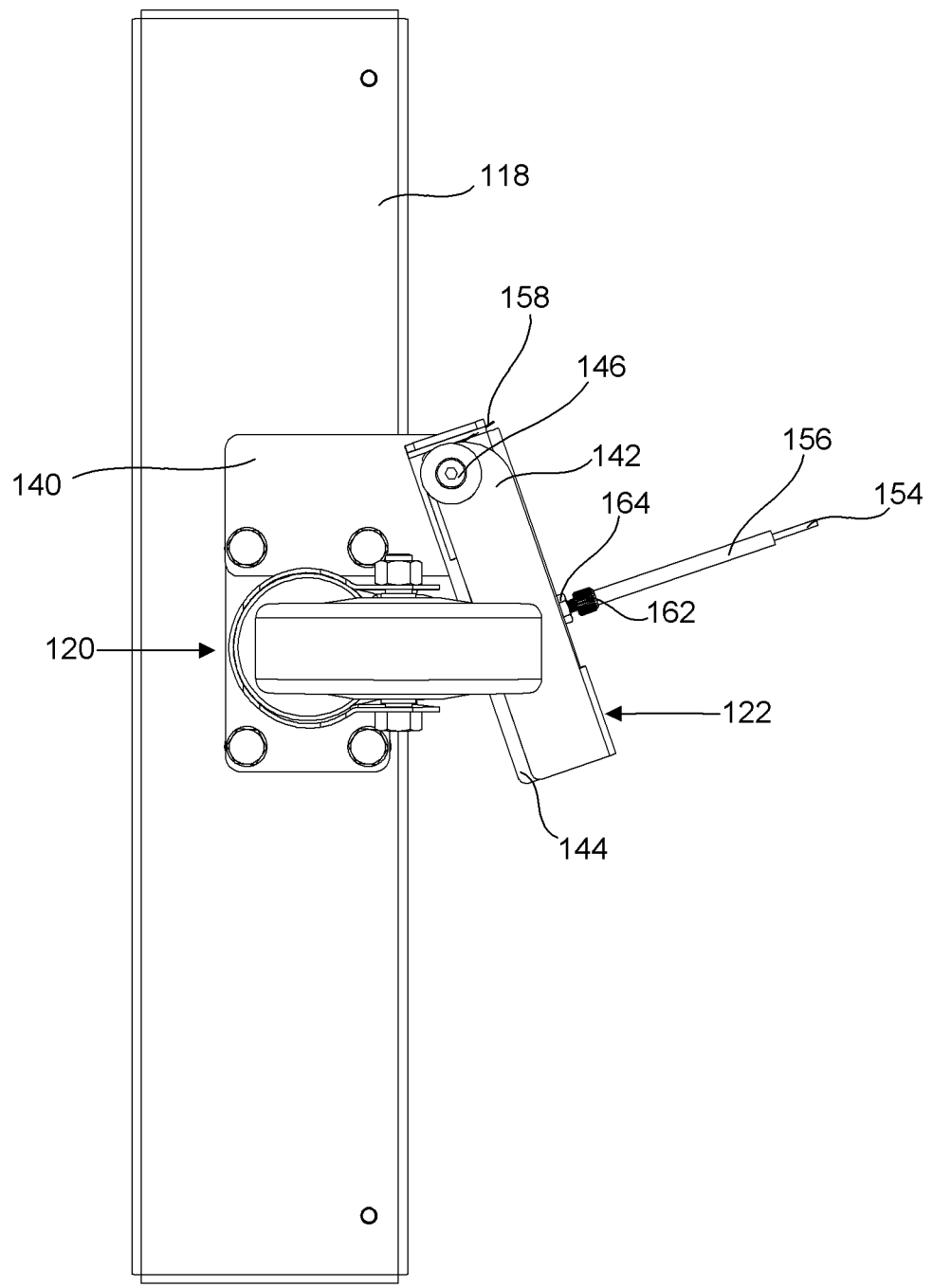
FIG. 7 is a bottom view of a caster direction-locking mechanism in accordance with an embodiment of the present invention and the auxiliary swivel caster assembly wheel assembly illustrated in FIGS. 4 through 6, shown in an unlocked position.

As best illustrated in FIG. 6, as noted above the top portion 128a of the horn 128 has a notch 128d formed therein. As will be explained below in detail, a locking member 152 of the caster direction-locking mechanism 122 releasably engages the notch 128d to selectively prevent or permit rotation of the horn 128 about the post 130 of the auxiliary swivel caster wheel assembly 120. When the notch is engaged to prevent rotation of the horn 128, the wheel 136 is constrained to rotate with its axis substantially parallel to the front of the cart.

Caster Direction-Locking Mechanism

First Embodiment

Figure 11:
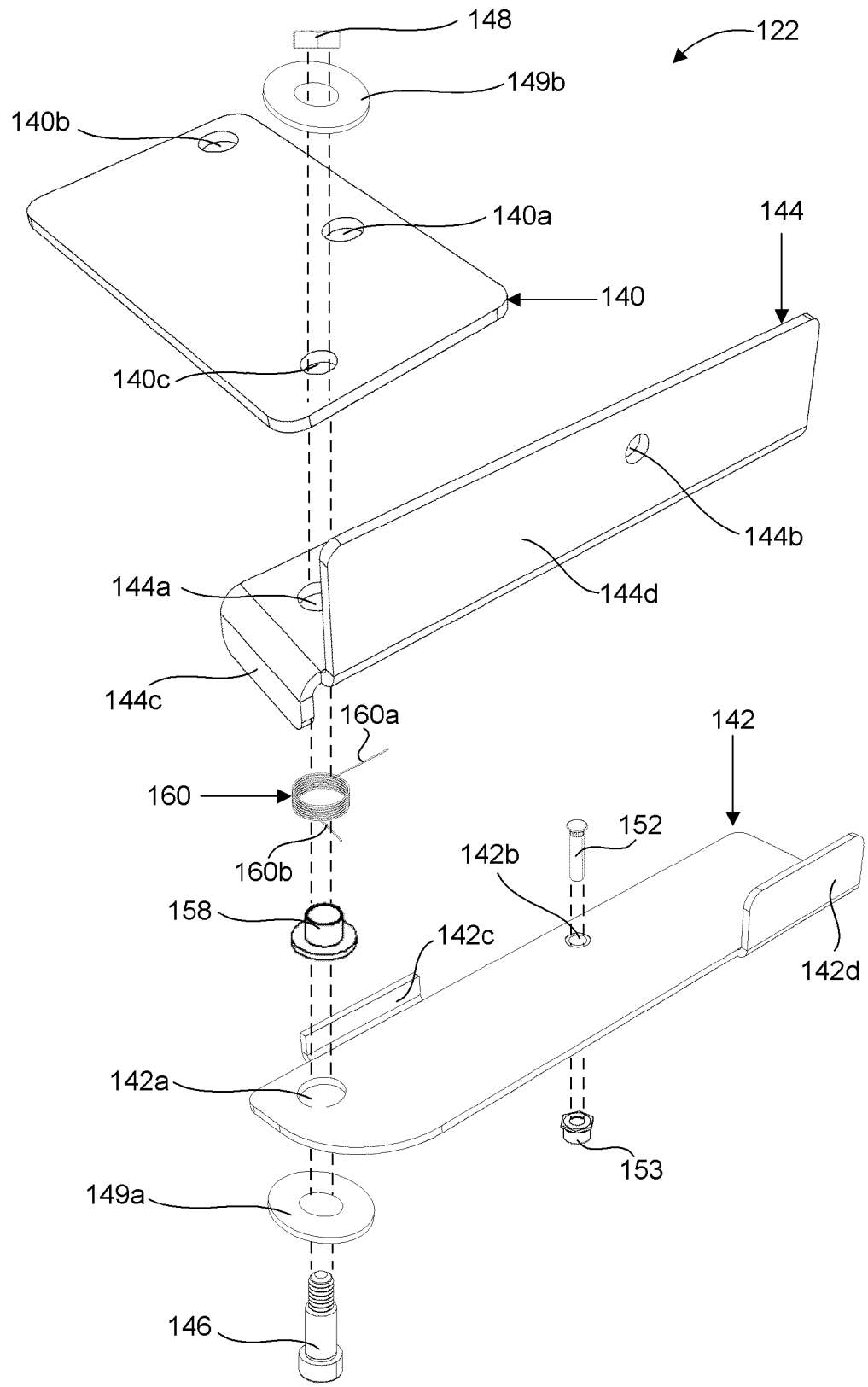
FIG. 11 is an exploded view of a portion of the caster direction-locking mechanism shown in FIGS. 7 through 10.
Figure 12:
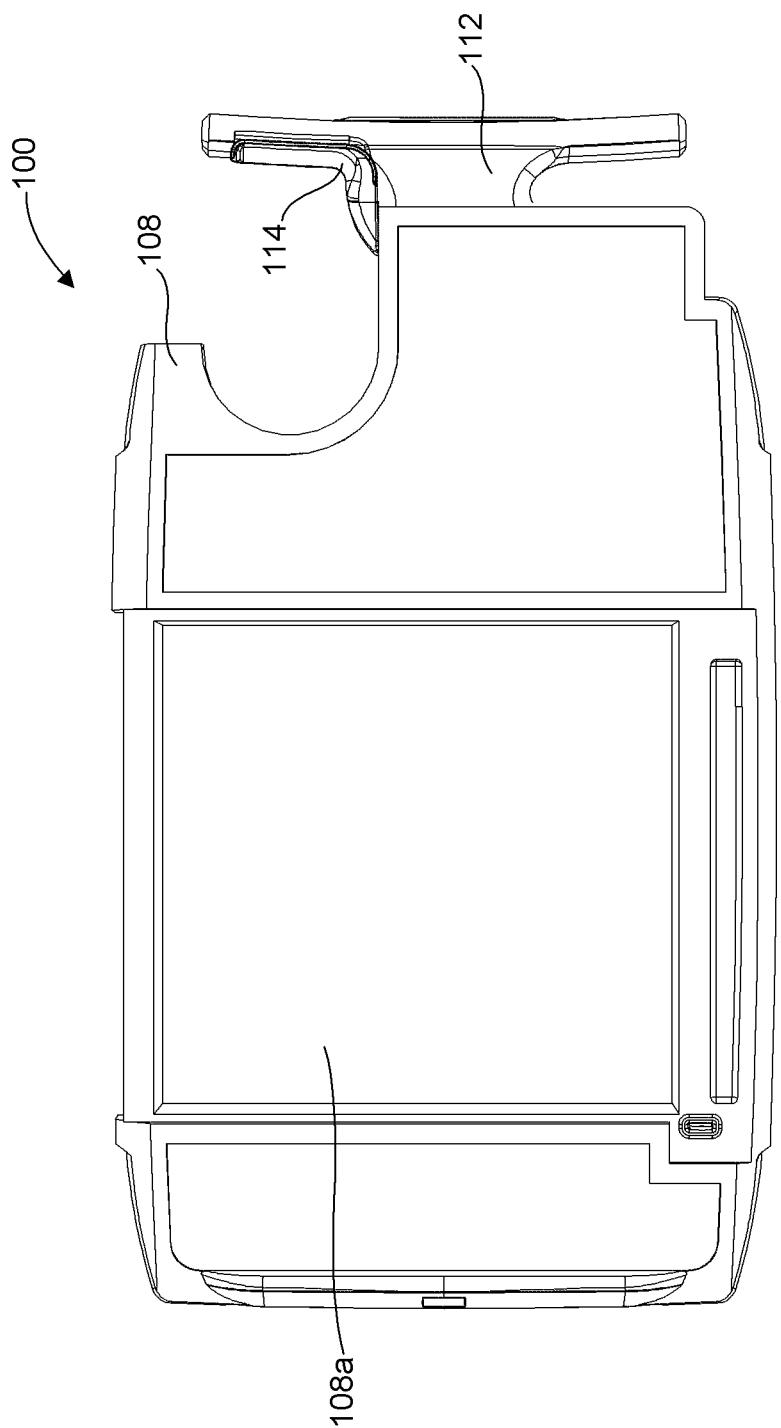
FIG. 12 is a top view the crash cart shown in FIG. 1.
Figure 13:
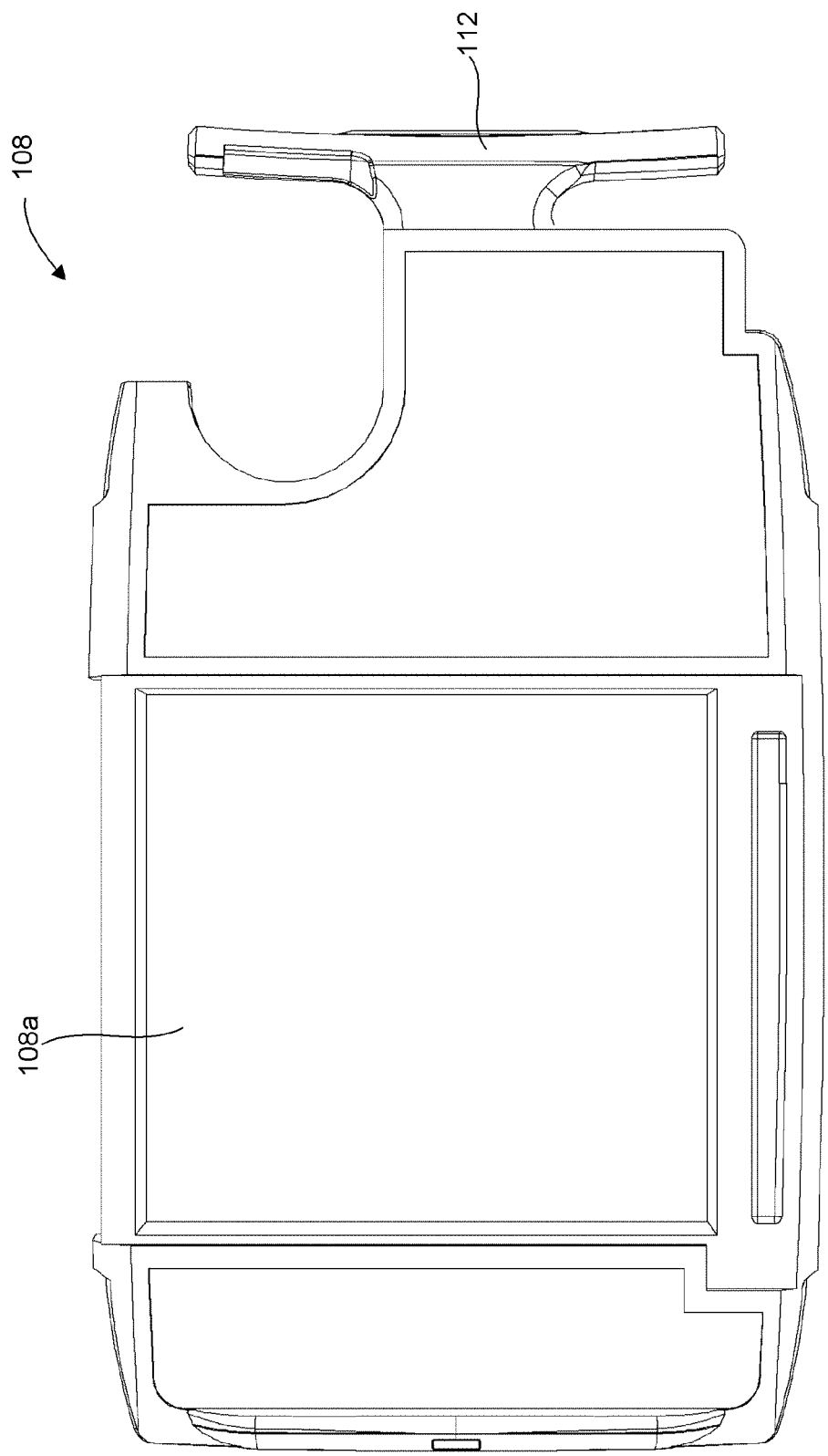
FIG. 13 is a top view of an upper member and a handle of the crash cart shown in FIG. 1.

An embodiment of the caster direction-locking mechanism 122 of the present invention is described with reference to FIGS. 7 through 19. A mounting plate 140 is provided to attach the caster direction-locking mechanism 122 to the auxiliary wheel support member 118. The mounting plate 140 includes three apertures 140a, 140b, and 140c formed therein, as shown in FIG. 11. A threaded end of a bolt (not labeled) is inserted into each of the apertures 140a and 140b, and through corresponding apertures (not shown) formed in the auxiliary wheel support member 118. A nut (not labeled) is securely attached to the threaded end of each of the bolts, thereby securing the mounting plate 140 to the auxiliary wheel support member 118.

The caster direction-locking mechanism 122 is pivotally attached to the mounting plate 140 using a shoulder screw 146 and a nut 148. More particularly, as best shown FIG. 11, a threaded end of the shoulder screw 146 is inserted through an aperture of a first washer 149a, an aperture 142a formed in a floating pin bracket 142, an aperture of a spacer 158, an aperture of a torsion spring 160, an aperture 144a of a swivel lock bracket 144, the aperture 140c of the mounting plate 140, and an aperture of a second washer 149b. A nut 148 is securely attached to the threaded end of the shoulder screw 146 thereby securing the shoulder screw 146, and thus, the caster direction-locking mechanism 122, to the mounting plate 140.

The floating pin bracket 142 also includes an aperture 142b formed therein. A first end of a locking member 152 is inserted through the aperture 142b of the floating pin bracket 142. A nut 153 is secured to threads formed on a portion of the locking member 152. As will be explained in detail below, actuation of the caster direction-locking mechanism 122 causes the locking member 152 to releasably engage the notch 128d of the top portion 128a of the horn 128 of the auxiliary swivel caster wheel assembly 120, when the notch 128d becomes aligned with the locking member 152.

The floating pin bracket 142 also includes a first flange 142c and a second flange 142d. When the caster direction-locking mechanism 122 is assembled, a first end 160a of the torsion spring 160 exerts a force on the first flange 142c of the floating pin bracket 142. Similarly, the swivel lock bracket 144 includes a first flange 144c and a second flange 144d. When the caster direction-locking mechanism 122 is assembled, a second end 160b of the torsion spring 160 exerts a force on the first flange 144c of the swivel lock bracket 144.

When the caster direction-locking mechanism 122 is assembled, the spacer 158 is disposed about a portion of the shoulder screw 146 having no threads thereon. The spacer 158 preferably is formed from nylon and permits the torsion spring 160 to rotate substantially unimpeded about the unthreaded portion of the shoulder screw 146.

The arrangement of the shoulder screw 146, the spacer 158, the torsion spring 160, the first flange 142c of the floating pin bracket 142, and the first flange 144c of the swivel lock bracket 144 cause the floating pin bracket 142 to be urged or biased towards the swivel lock bracket 144 until the second flange 142d of the floating pin bracket 142 contacts the second flange 144d of the swivel lock bracket 144. As will be described below, the mentioned arrangement causes the locking member 152 to engage smoothly the notch 128d of the top portion 128a of the horn 128, when the caster direction-locking mechanism 122 is activated.

As shown in FIGS. 7-10, 18, and 19, a cable 154 is provided within a cable housing 156. The cable 154 and the cable housing 156 in conjunction with a trigger mechanism 114, cause the caster direction-locking mechanism 122 to rotate about the shoulder screw 146 so as to releasably engage the locking member 152 in notch 128d the top portion 128a of the horn 128.

Figure 8:
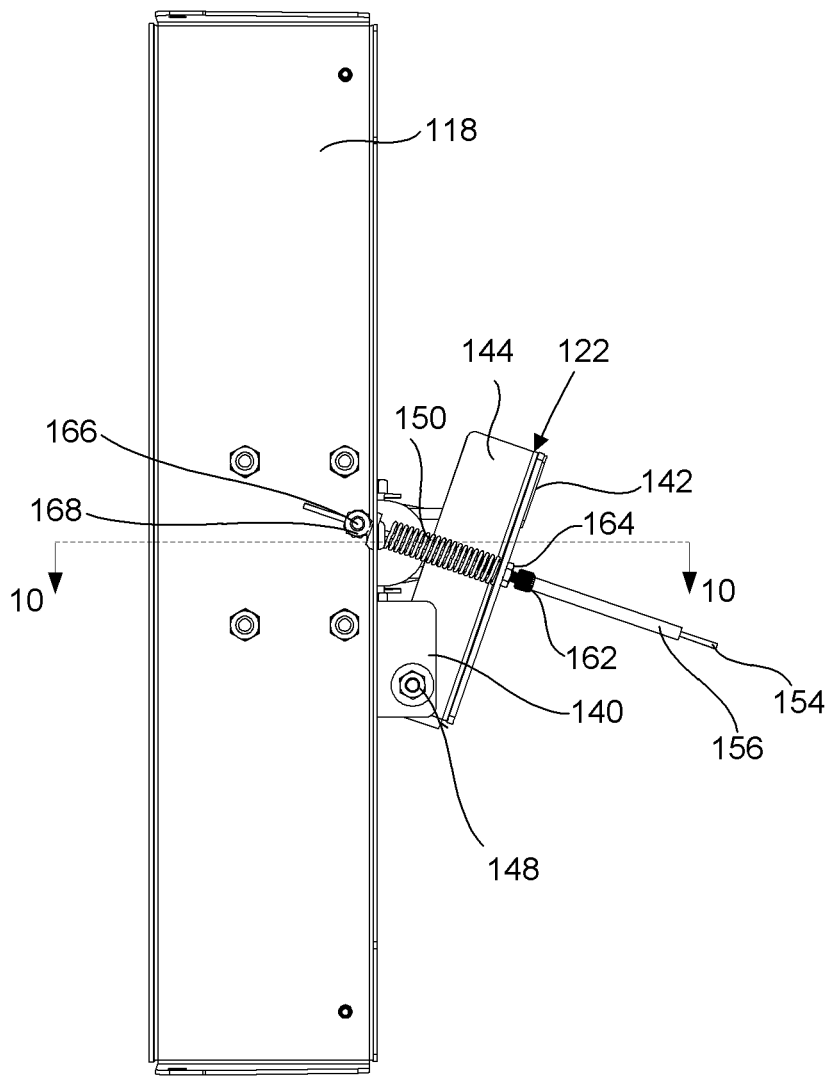
FIG. 8 is a top view of the caster direction-locking mechanism and the auxiliary swivel caster wheel assembly illustrated in FIG. 7.

As shown in FIG. 11, the swivel lock bracket 144 includes a second aperture 144b formed in the second flange 144d. As shown in FIG. 8, for example, the first end of a barrel adjuster bolt 162 is inserted through the second aperture 144b of the swivel lock bracket 144, and a nut (not shown) is secured thereto. A barrel adjuster nut 164 is positioned on an opposing second end of the barrel adjuster bolt 162 and advanced until it contacts the second flange 144d, as shown in FIG. 8, for example. A first end of the cable housing 156 is attached to the second end of the barrel adjuster bolt 162. The barrel adjuster bolt 162 enables a distance between the second flange 144d of the swivel lock bracket 144 and the first end of the cable housing 156 to be adjusted. The barrel adjuster bolt 162 and barrel adjuster nut 164 are adjusted in a manner that is similar to adjusting a cable of a bicycle caliper brake system.

As shown in FIG. 8, a first end of the cable 154 is inserted through the barrel adjuster bolt 162 and a tension spring 150 prior to being attached to the auxiliary wheel support member 118. A bolt 166 includes an aperture (not shown) formed in a threaded portion thereof. The bolt 166 is inserted through an aperture (not shown) of the auxiliary wheel support member 118, and the first end of the cable 154 is inserted through another aperture (not shown) of the auxiliary wheel support member 118 and through the aperture of the bolt 166. A nut 168 is securely attached to the bolt 166 thereby clamping the first end of the cable 154 to the auxiliary wheel support member 118.

Trigger Mechanism

Figure 14:
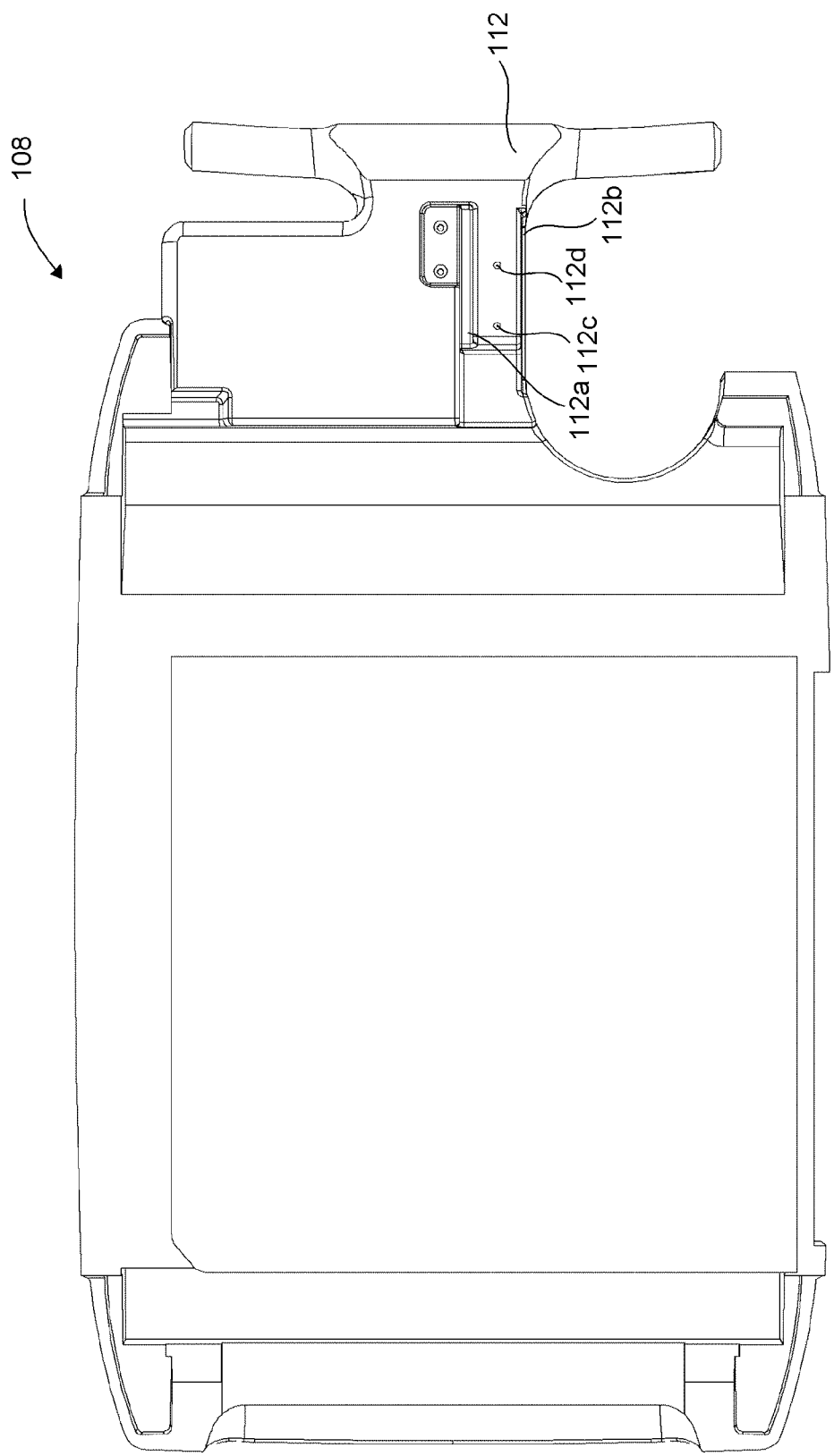
FIG. 14 is a bottom view of the upper member and the handle shown in FIG. 13.
Figure 15:
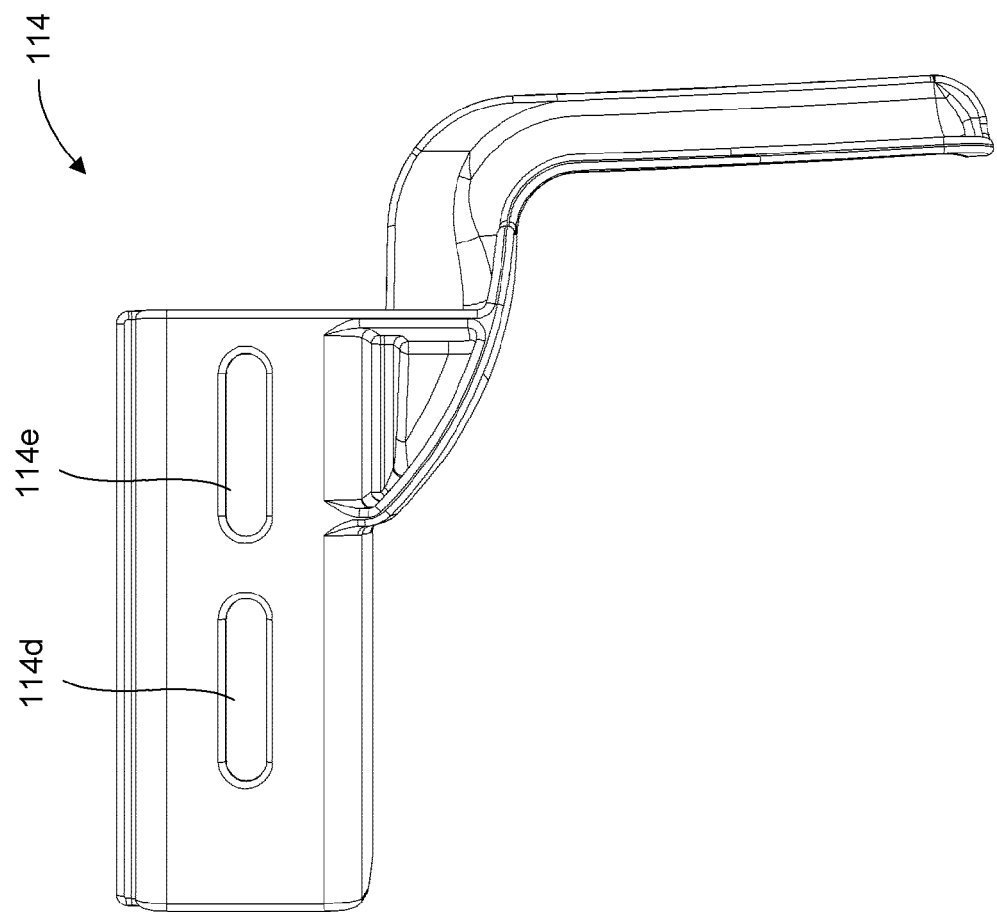
FIG. 15 is a bottom view of a trigger mechanism according to an embodiment of the present invention.
Figure 16:
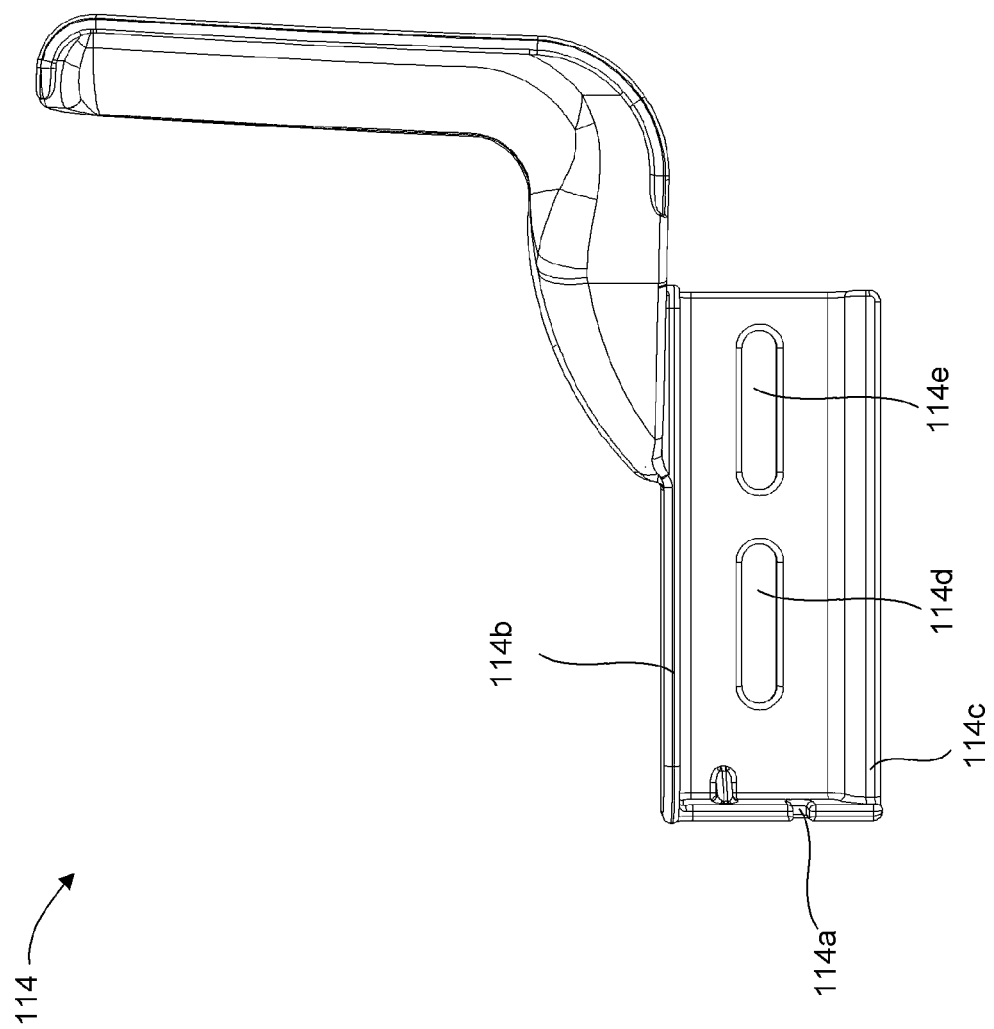
FIG. 16 is a top view of the trigger mechanism shown in FIG. 15.
Figure 17:
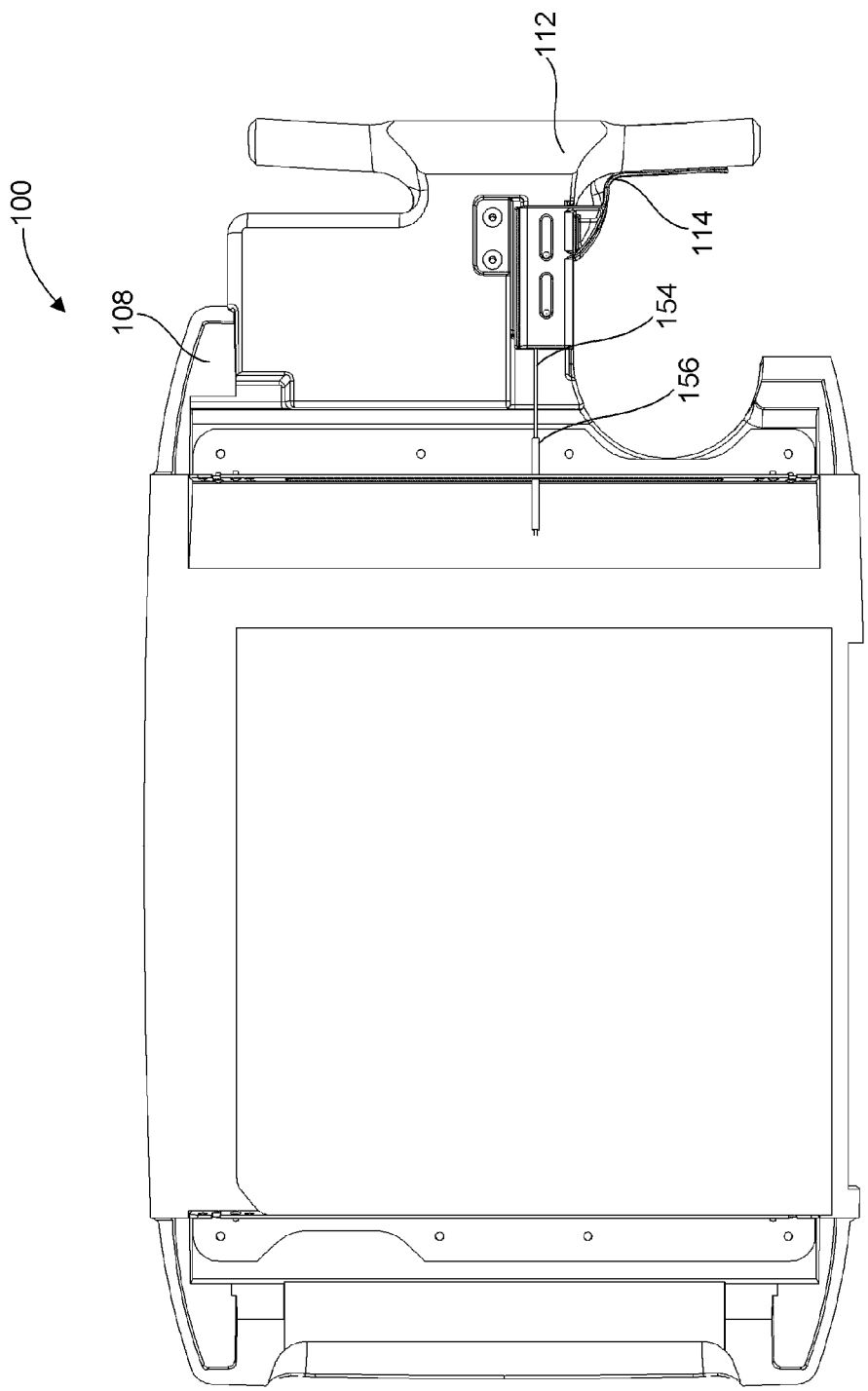
FIG. 17 is a bottom view of the upper member, the handle, and the trigger mechanism of the crash cart shown in FIG. 1.

As shown in FIG. 14, a bottom side of the handle 112 includes a first flange 112a, a second flange 112b, and apertures 112c and 112d. As shown in FIG. 16, a top side of the trigger mechanism 114 includes a notch 114a, a first side member 114b that forms a first groove, a second side member 114c that forms a second groove, and elongated apertures 114d and 114e.

Attachment of the cable 154 and the trigger mechanism 114 to the handle 112 is described with reference to FIGS. 14 through 17. A cable stop (not shown) is secured to the second end of the cable 154. The cable stop is similar to cable stops that are attached to conventional bicycle brake cable wires. The second end of the cable 154 is placed in the notch 114a such that the cable stop is disposed within the trigger mechanism 114.

The top side of the trigger mechanism 114 is placed in contact with the bottom side of the upper member 108 such that the first groove formed by the first side member 114b of the trigger mechanism 114 is disposed about the second flange 112b of the handle 112, and the second groove formed by the second side member 114c of the trigger mechanism 114 is disposed about the first flange 112a of the handle 112. A screw (not shown) is inserted through each the elongated apertures 114d and 114e of the trigger mechanism 114, and these screws are secured within the apertures 112c and 112d of the handle 112, respectively. The trigger mechanism is now slidably attached to the handle 112.

Accordingly, the first ends of the cable 154 and the cable housing 156 are connected to the locking mechanism 122 and the second ends of the cable 154 and the cable housing 156 are connected to the trigger mechanism 114. Portions of the cable 154 and the cable housing 156 between the first ends and the second ends are disposed within the cart 100. For example, such portions are housed in a hollow, center portion of a panel (not shown) that is attached to the trailing end of the cart, i.e., the end where the handle 112 is provided.

Actuation of the Caster Direction-Locking Mechanism

As noted above, the wheel 136 of the caster assembly 120 is always urged toward a supporting floor by springs 121.

Figure 9:
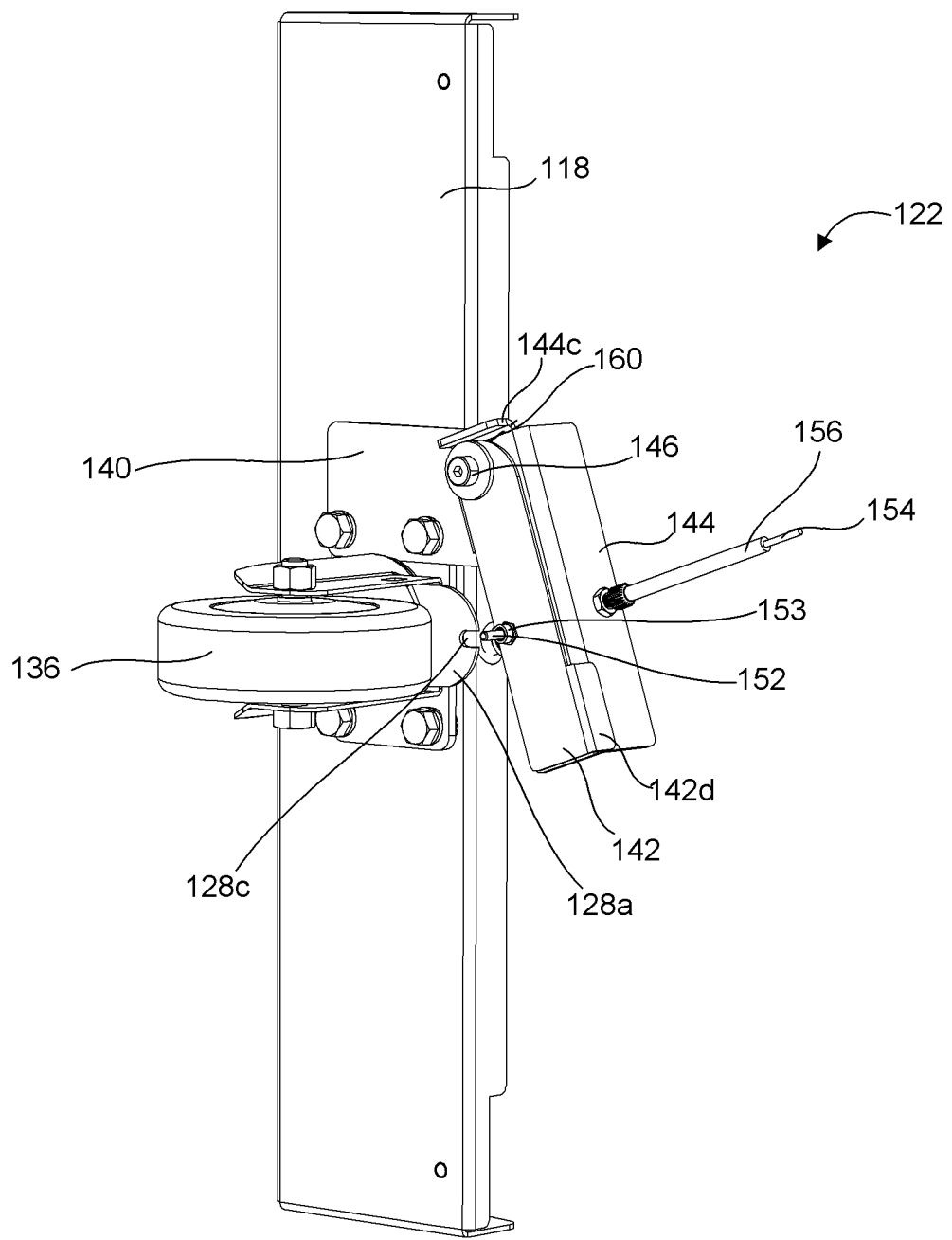
FIG. 9 is a perspective view taken from the bottom of the caster direction-locking mechanism and the auxiliary swivel caster wheel assembly illustrated in FIG. 7.
Figure 10:
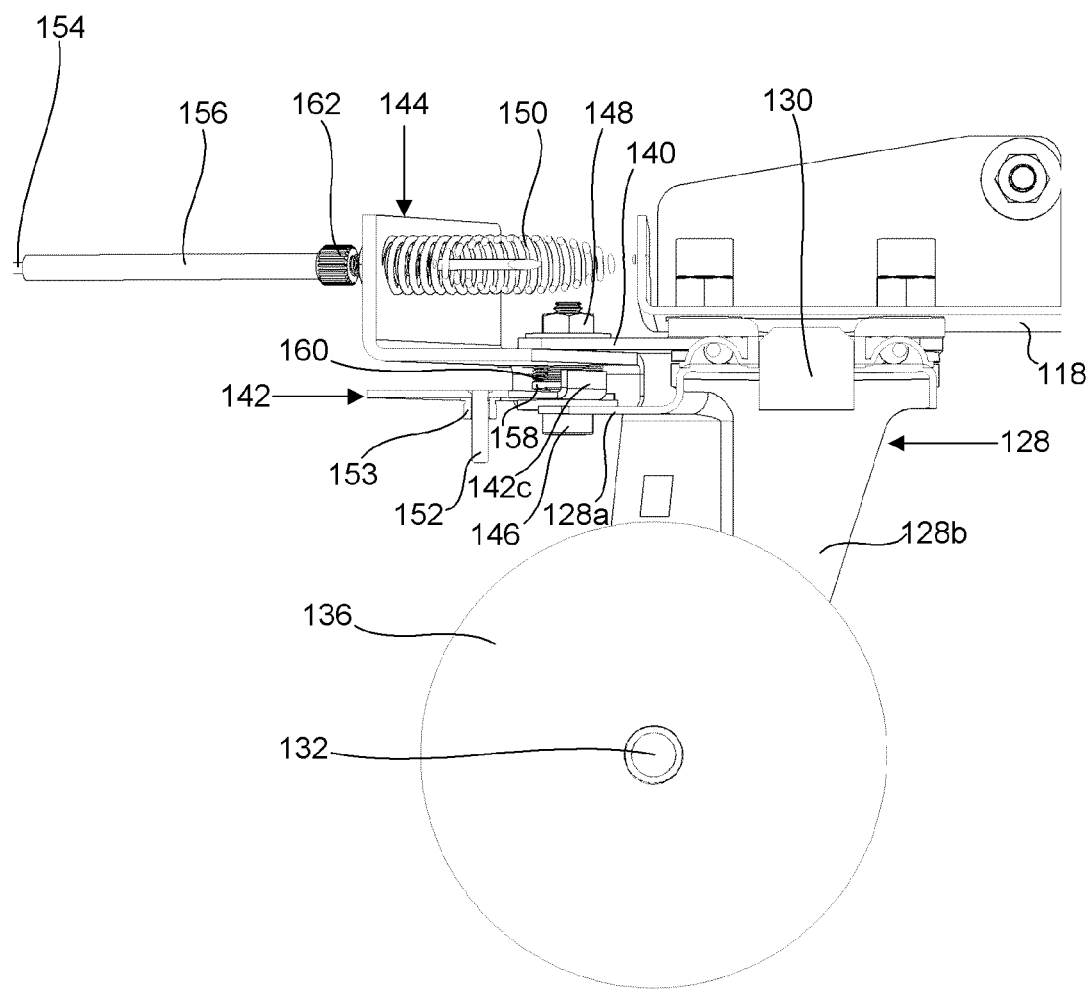
FIG. 10 is a vertical cross-sectional view of the caster direction-locking mechanism and the auxiliary swivel caster wheel assembly illustrated in FIG. 8, partly shown in phantom, as viewed from plane 10 in the direction of the arrows shown in FIG. 8.

Further, when the trigger mechanism 114 is not actuated by a user, a biasing force of the tension spring 150 urges the swivel lock bracket 144 away from the auxiliary swivel caster wheel assembly 120, as shown in FIGS. 7 through 10. In addition, the second flange 144d of the swivel lock bracket 144 exerts a force on the second flange 142d of the floating pin bracket 142, which causes the floating pin bracket 142 also to be urged away from the auxiliary swivel caster wheel assembly 120. When the swivel lock bracket 144 and the floating pin bracket 144 are urged away from the auxiliary swivel caster wheel assembly 120 via the tension spring 150, the locking member 152 does not engage the notch 128d of the upper portion 128a of the horn 128, as shown in FIG. 9. Accordingly, when the trigger mechanism 114 is not actuated by a user, the horn 128, and thus the wheel 136, are permitted to rotate freely about the post 130 of the auxiliary swivel caster wheel assembly 120. Even though the wheel 136 is in contact with the floor, the cart may be moved as all five wheels may swivel.

When a user pulls the trigger mechanism 114 in a direction toward the user, the notch 114a of the trigger mechanism 114 exerts a force on the cable stop attached to the second end of the cable 154 thereby causing the second end of the cable 154 to move in the direction toward the user, which activates the caster direction-locking mechanism 122. When the user releases the trigger mechanism 114, the caster direction-locking mechanism 122 causes the cable stop attached to the second end of the cable 154 to exert a force on notch 114a of the trigger mechanism 114 in a direction away from the user, which causes the trigger mechanism 114 to return to its original position on the handle 112.

When a user actuates the trigger mechanism 114, the first end of the cable housing 156 is urged toward the auxiliary swivel caster wheel assembly 120. Because the first end of the cable housing 156 is secured to the second flange 144d of the swivel lock bracket 144 via the barrel adjuster bolt 162, actuation of the trigger mechanism 114 causes the swivel lock bracket 144 to be urged toward the auxiliary swivel caster wheel assembly 120. As described above, the torsion spring 160 urges the floating pin bracket 142 toward the swivel lock bracket 144. Accordingly, when the swivel lock bracket 144 is urged toward the auxiliary swivel caster wheel assembly 120 by actuation of the trigger mechanism 114, the floating pin bracket 142 also is urged toward the auxiliary swivel caster wheel assembly 120.

Figure 18:
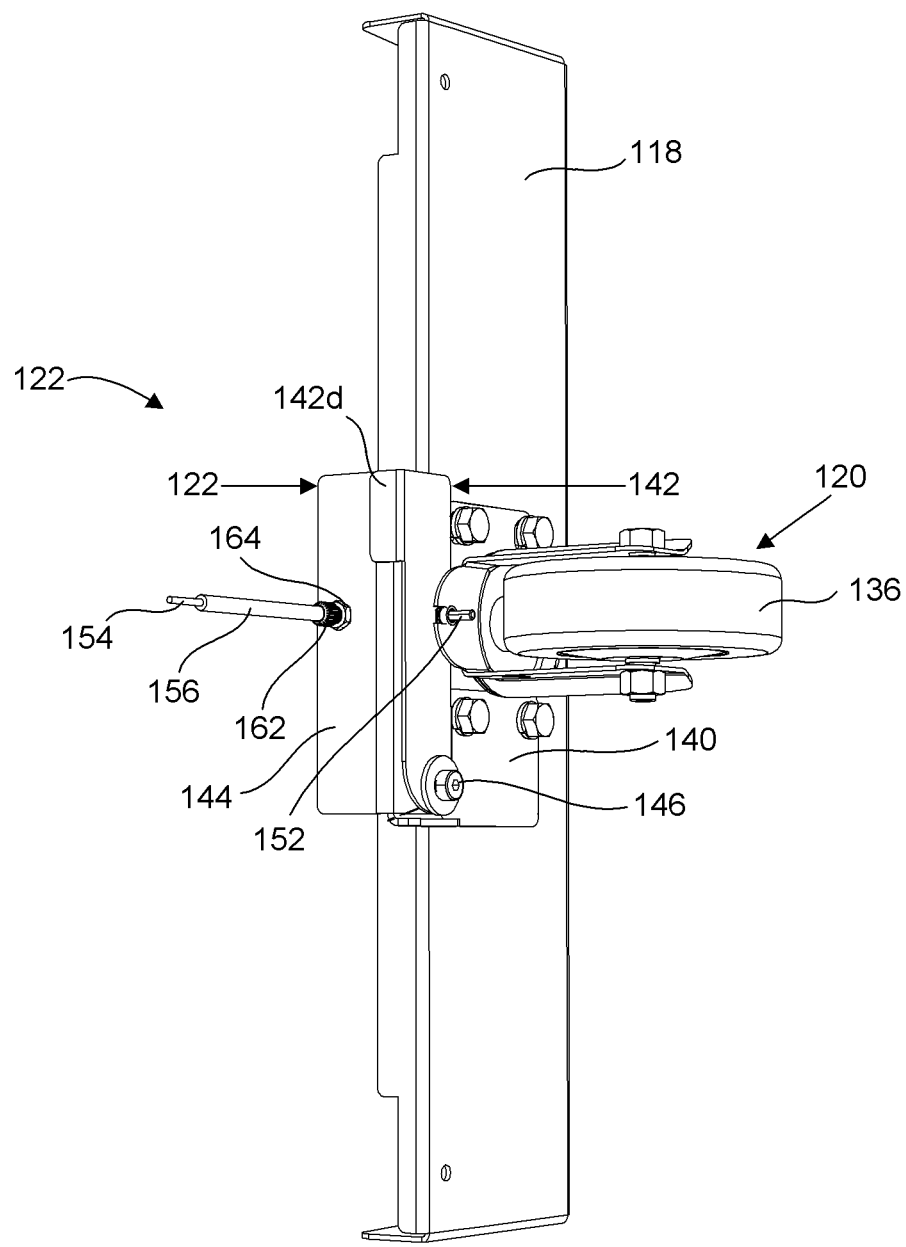
FIG. 18 is a perspective view of the caster direction-locking mechanism and the auxiliary swivel caster wheel assembly illustrated in FIGS. 7 through 10, shown in a locked position.
Figure 19:
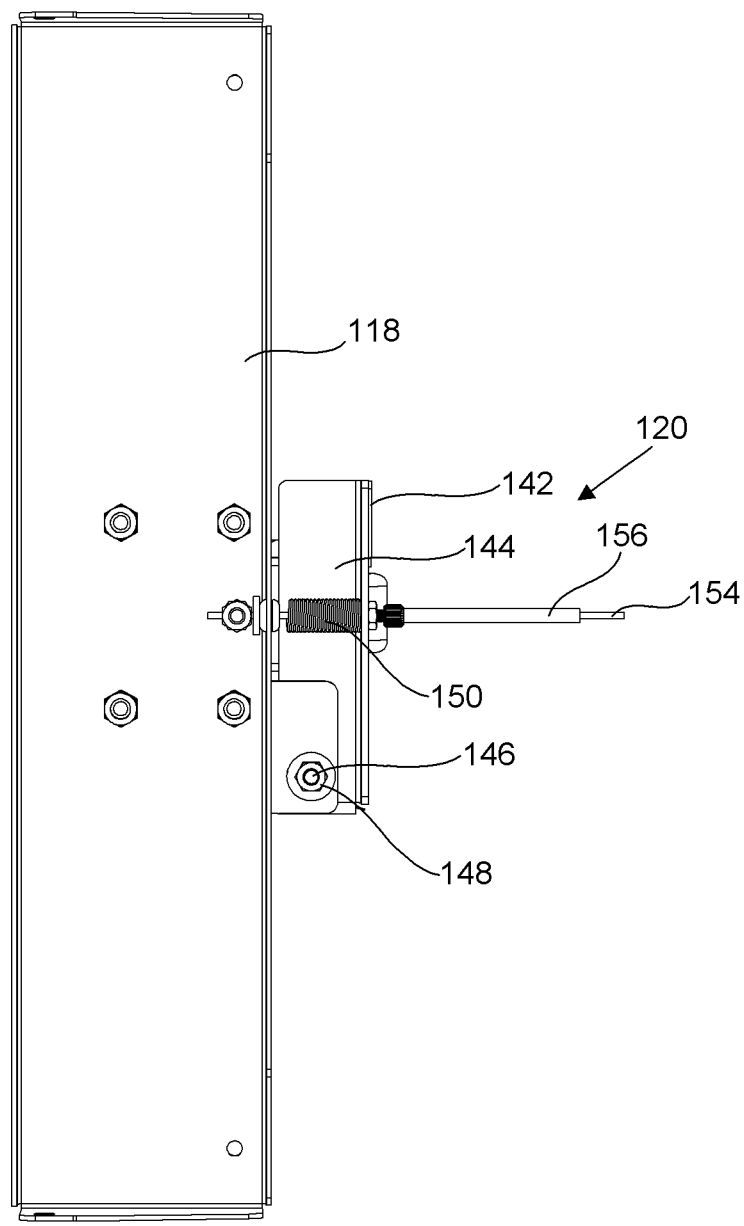
FIG. 19 is a top view of the caster direction-locking mechanism shown in FIG. 18.

If the notch 128d is not aligned with the locking member 152 when the trigger mechanism 114 is actuated, the top portion of the 128a of the horn 128 will contact the locking member 152 and inhibit the floating pin bracket 142 from meeting the swivel lock bracket 144. As the cart 100 is moved, the horn 128 rotates about the post 130 and the notch 128d of the horn 128 becomes aligned with the locking member 152 of the floating pin bracket 142. The biasing force of the torsion spring 160 causes the locking member 152 of the floating pin bracket 142 to engage the notch 128d, when the notch 128 becomes aligned with the locking member 152, as shown in FIG. 18. As shown in FIG. 6, the upper portion 128a has a round shape which facilitates engagement of the locking member 152 into the notch 128d as the horn 128 rotates. The torsion spring 160 enables the floating pin bracket 142 to be spaced apart from the swivel lock bracket 144 as the horn 128 rotates to a predetermined position where the locking member 152 and the notch 128d are aligned.

Engagement of the locking member 152 into the notch 128d prevents the horn 128 from rotating about the post 130 of the auxiliary swivel caster wheel assembly 120. The notch 128d is disposed on the horn 128 such that the wheel 136 of the auxiliary swivel caster wheel assembly 120 is held in a predetermined position, which is preferably substantially parallel to horizontal base members 104b and 104d, when the locking member 152 engages the notch 128d. Accordingly, when a user actuates the trigger mechanism 114, the horn 128, and thus the wheel 136, are prevented from rotating about the post 120, thereby providing a firm pivot for steering and maneuvering the cart 100.

For example, if a user actuates the trigger mechanism 114 just before attempting to steer the cart 100 around a corner, the fixed position of the wheel 136 of the auxiliary swivel caster wheel assembly 120 provides a firm pivot that enables the cart 100 to round the corner without overturning and without the user otherwise loosing control of the cart 100. The user would likely release the trigger mechanism 114 when maneuvering the cart 100 in a patient's room, which enables the tension spring 150 to cause the locking member 152 to disengage from the notch 128d, thereby permitting the horn 128, and thus the wheel 136, to rotate freely about the post 130.

The above-described arrangement of the floating pin bracket 142 and the notch 128d, advantageously prevents the locking member 152 from causing the horn 128 to stop rotating in any position other than a position in which the locking member 152 is aligned with the notch 128d. That is, if the locking member 152 were attached directly to the swivel lock bracket 144, actuation of the trigger mechanism 114 would likely cause the horn 128 to stop rotating when the horn 128 is positioned at a random orientation, which would degrade steering and maneuverability of the cart 100.

Caster Direction-Locking Mechanism

Second Embodiment

Figure 20:
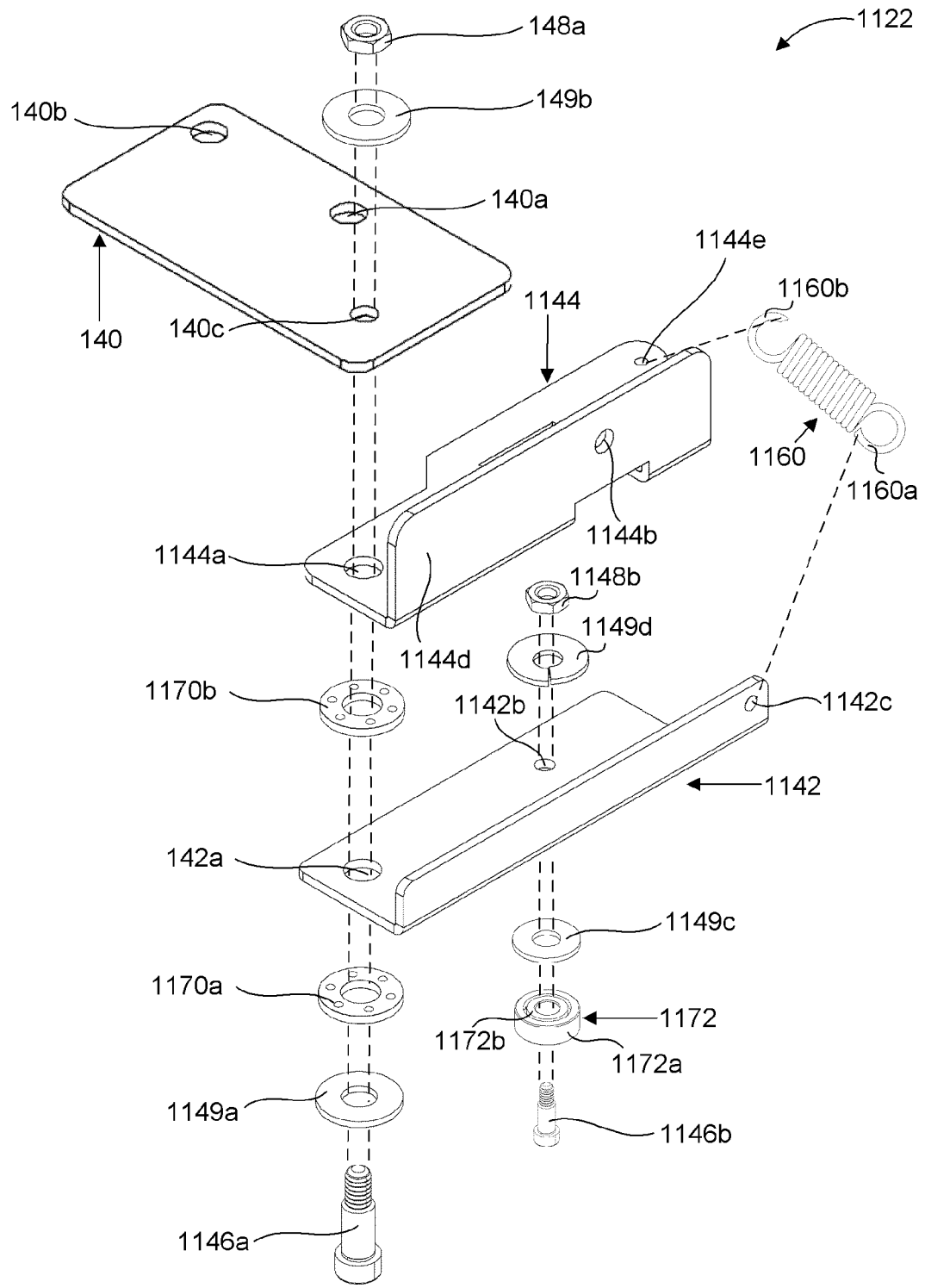
FIG. 20 is an exploded view of a portion of a caster direction-locking mechanism according to a second embodiment of the present invention.

FIG. 20 illustrates an exploded view of a second embodiment of a caster direction-locking mechanism 1122 of the present invention. The caster direction-locking mechanism 1122 operates in a similar fashion to the caster direction-locking mechanism 122 described above.

The caster direction-locking mechanism 1122 is pivotally attached to the mounting plate 140 using a shoulder screw 1146a and a first nut 1148a. More particularly, a threaded end of the shoulder screw 1146a is inserted through an aperture of a first washer 1149a, an aperture of a first thrust bearing 1170a, an aperture 1142a formed in a floating pin bracket 1142, an aperture of a second thrust bearing 1170b, an aperture 1144a of a swivel lock bracket 1144, the aperture 140c of the mounting plate 140, and an aperture of a second washer 1149b. The first nut 1148a is securely attached to the threaded end of the first shoulder screw 1146a thereby securing the first shoulder screw 1146a, and thus the caster direction-locking mechanism 1122, to the mounting plate 140. The first thrust bearing 1170a and the second thrust bearing 1170b enable the floating pin bracket 1142 to pivot freely about the first shoulder screw 1146a.

A threaded end of a second shoulder screw 1146b is inserted into an aperture of a bearing assembly 1172, an aperture of a third washer 1149c, an aperture 1142b of the floating pin bracket 1142, and an aperture of a fourth washer 1149d. A second nut 1148b is secured to the threaded end of the second shoulder screw 1146b. The bearing assembly 1172 includes an outer portion 1172a and an inner portion 1172b, which are separated by a plurality of ball bearings (not illustrated). When the bearing assembly 1170 is secured to the floating pin bracket 1142, the outer portion 1172a is enabled to rotate freely about a vertical axis, i.e., the second shoulder screw 1146b.

A tension spring 1160 is employed to urge the floating pin bracket 1142 toward the swivel lock bracket 1144. More particularly, a first end 1160a of the tension spring 1160 is inserted into an aperture 1142c formed through the floating pin bracket 1142, which secures the tension spring 1160 to the floating pin bracket 1142. A second end 1160b of the tension spring 1160 is inserted into an aperture 1144e formed through the swivel lock bracket 1144, which secures the tension spring 1160 to the swivel lock bracket 1144.

The barrel adjuster bolt 162 is secured to an aperture 1144b formed in a flange 1144d of the swivel lock bracket 1144. The first end of the cable 154 is inserted through the barrel adjuster bolt 162 prior to being attached to the auxiliary wheel support member 118, as described above for the caster direction-locking mechanism 122. Accordingly, actuation of the trigger mechanism 114 causes the swivel lock bracket 1144 to move toward the auxiliary wheel support member 118, as described above for the caster direction-locking mechanism 122.

Auxiliary Swivel Caster Wheel Assembly

Second Embodiment

Figure 21:
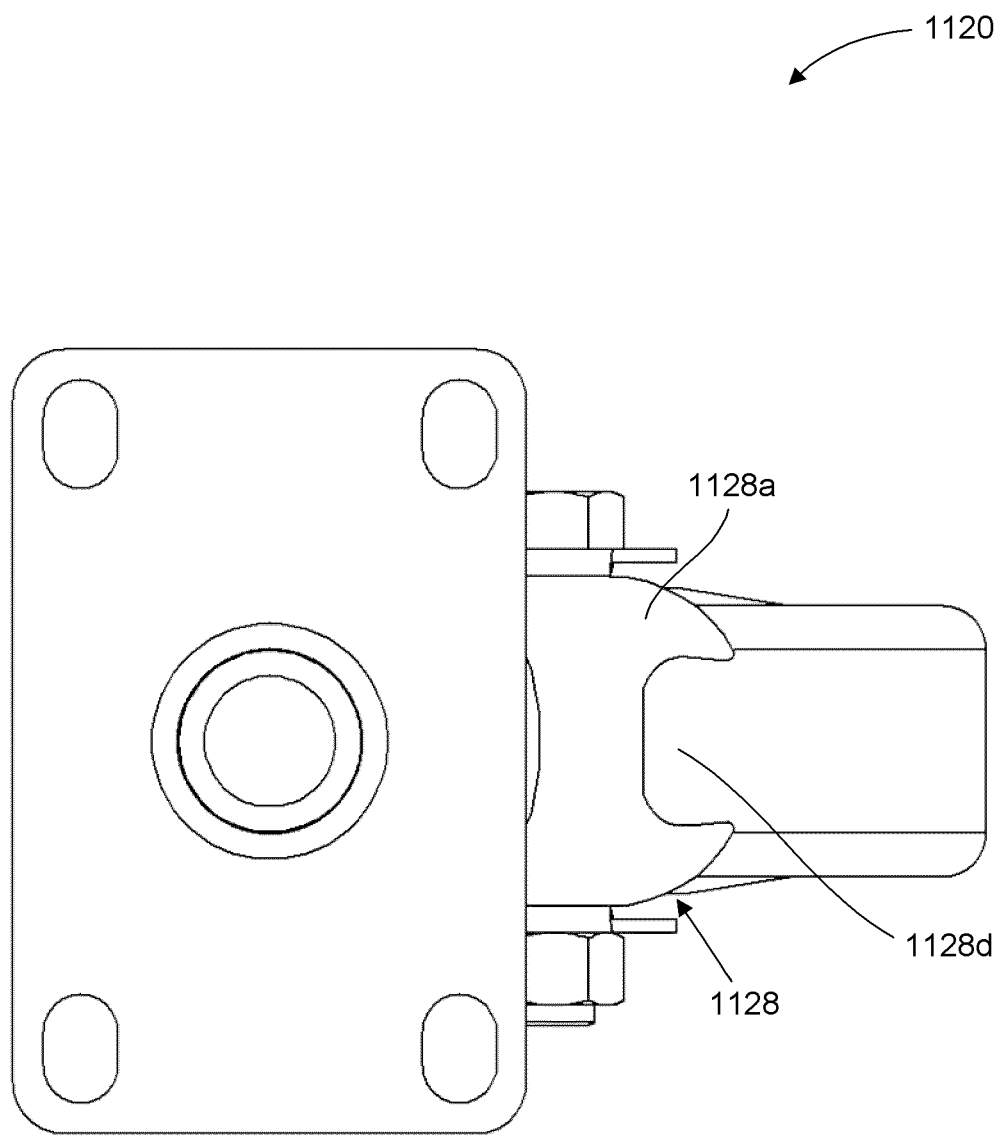
FIG. 21 is a top view an auxiliary swivel caster wheel assembly according to a second embodiment of the present invention.

FIG. 21 illustrates a top view of a second embodiment of an auxiliary swivel caster wheel assembly 1120 of the present invention. The swivel caster wheel assembly 1120 operates in a similar fashion to the caster direction-locking mechanism 120 described above. The swivel caster wheel assembly 1120 includes a horn 1128 having a top portion 1128a that has a notch 1128d formed therethrough. The notch 1128d of the swivel caster wheel assembly 1120 shown in FIG. 21 is deeper and wider than the notch 128d of the swivel caster wheel assembly 120 shown in FIG. 6. The shape of the notch 1128d enables the outer portion 1172a of the bearing assembly 1172 to engage the notch 1128d, when the trigger mechanism 114 is actuated.

As described above, the outer portion 1172a of the bearing assembly 1172 is enabled to rotate freely about the second shoulder screw 1146b. When the trigger mechanism 114 is actuated, the swivel lock bracket 1144 is urged toward the auxiliary swivel caster wheel assembly 1120. The tension spring 1160 enables the floating pin bracket 1142 to be spaced apart from the swivel lock bracket 1144 as the horn 1128 rotates to a predetermined position. The tension spring 1160 urges the floating pin bracket 1142 toward the swivel lock bracket 1144 as the horn 1128 rotates to the predetermined position, which causes the outer portion 1172a of the bearing assembly 1172 to contact the curved top portion 1128a of the horn 1128 and rotate, as the horn 1128 rotates to the predetermined position. When the bearing assembly 1172 becomes aligned with the notch 1128d at the predetermined position, the tension spring 1160 causes the bearing assembly 1172 to engage the notch 1128d of the horn 1128, which prevents the swivel caster wheel assembly 1120 from rotating about its vertical axis. The arrangement described above advantageously enables the bearing assembly 1172 of the caster direction-locking mechanism 1122 to engage smoothly the notch 1128d of the horn 1128 of the swivel caster wheel assembly 1120.

While the present invention has been described with respect to what is presently considered to be the preferred embodiments, the present invention is not limited to the disclosed embodiments. Rather, the present invention covers various modifications and equivalent arrangements included within the spirit and scope of the appended claims. The scope of the appended claims is to be accorded the broadest interpretation so as to encompass all such modifications and equivalent structures and functions.

What is claimed is:

1. A cart having a first end and a second end, said cart comprising:
at least four swivel casters supporting said cart, a first two of said swivel casters being adjacent to each other and supporting said cart in the region of said first end, and a second two of said swivel casters being adjacent to each other and supporting said cart in the region of said second end, each said swivel caster including a wheel rotatable about a horizontal axis and being mounted with said cart for swiveling movement about a generally vertical axis;
an auxiliary support member disposed between said first end and said second end;
an auxiliary swivel caster assembly supporting said cart, said auxiliary swivel caster assembly including:
an auxiliary wheel rotatable about a horizontal axis, and
a locking member receiving portion,
wherein said auxiliary wheel is swivelable about a generally vertical axis;
a mounting plate connected to said auxiliary support member;
a locking unit pivotably coupled to said mounting plate, said locking unit including:
a bracket comprising a locking member, and
a tension spring disposed between said bracket and said auxiliary support member so as to bias said bracket about a generally vertical axis and away from said auxiliary support member,
wherein said locking member selectively engages and disengages said locking member receiving portion, and
wherein, to engage said locking member receiving portion, said bracket pivots about the generally vertical axis and toward said auxiliary swivel caster assembly such that said locking member engages said locking member receiving portion when said auxiliary wheel of said auxiliary swivel caster assembly swivels to a predetermined position.

2. The cart according to claim 1, further comprising:
an actuation unit for selectively engaging and disengaging said locking member and said locking member receiving portion; and
a handle for steering said cart mounted at said first end, wherein said actuation unit is disposed adjacent said handle.

3. The cart according to claim 1,
wherein when said locking member disengages from said locking member receiving portion, said tension spring biases said bracket away from said auxiliary support member to permit swiveling movement of said auxiliary wheel.

4. The cart according to claim 1, wherein said auxiliary swivel caster assembly further includes a horn disposed about said auxiliary wheel of said auxiliary swivel caster assembly, wherein said horn includes a notch formed therein as the locking member receiving portion, and wherein said locking member engages the notch when said tension spring is compressed and said bracket pivots about the generally vertical axis and toward said auxiliary swivel caster assembly.

5. The cart according to claim 1, further comprising:
a base portion; and
a storage structure supported by said base portion.

6. The cart according to claim 1, wherein said locking unit selectably locks said auxiliary wheel against swiveling movement when said auxiliary wheel of said auxiliary swivel caster assembly swivels to the predetermined position, which is substantially perpendicular to said first end.

7. The cart according to claim 1, wherein said cart includes a third end and a fourth end, and wherein said auxiliary swivel caster assembly is disposed closer to said third end than to said fourth end.

8. The cart according to claim 1, further comprising:
a third end substantially perpendicular to said first end and to said second end; and
a fourth end substantially parallel to said third end;
wherein said auxiliary swivel caster assembly is disposed substantially midway between said third end and said fourth end.

9. A cart according to claim 1, further comprising:
a plurality of comparison springs disposed between a bottom surface of said cart and said auxiliary support member such that said auxiliary support member is biased away from said bottom surface and toward a floor supporting said cart.

10. A cart comprising:
a base portion;
a pair of leading end swivel casters supporting said base portion, each of the pair of leading end swivel casters including a rotatable wheel;
a pair of trailing end swivel casters supporting said base portion, each of the pair of trailing end swivel casters including a rotatable wheel;
an auxiliary support member disposed between said pair of leading end swivel casters and said pair of trailing end swivel casters and pivotably connected to said base portion;
an auxiliary swivel caster assembly supporting said base portion, said auxiliary swivel caster assembly including:
a rotatable auxiliary wheel, and
a locking member receiving portion,
wherein said auxiliary wheel is swivelable about a substantially vertically extending axis;
a mounting plate connected to said auxiliary support member;
a comparison spring connected to said base portion and said auxiliary support member, and arranged such that said auxiliary support member is biased away from said base portion and said auxiliary wheel is urged toward a floor supporting said cart;
a locking mechanism pivotably coupled to said mounting plate, said locking mechanism including:
a bracket comprising a locking member; and
a tension spring disposed between said bracket and said auxiliary support member so as to bias said bracket about a generally vertical axis and away from said auxiliary support member,
wherein said locking member selectively engages and disengages said locking member receiving portion, and
wherein, to engage said locking member receiving portion, said bracket pivots about the generally vertical axis and toward said auxiliary swivel caster assembly such that said locking member engages said locking member receiving portion when said auxiliary wheel of said auxiliary swivel caster assembly swivels to a predetermined position.

11. The cart according to claim 10, further comprising:
an actuation mechanism for selecting engaging and disengaging said locking member and said locking member receiving portion; and a handle for steering said cart, wherein said actuation mechanism is disposed adjacent said handle.

12. The cart according to claim 10,
wherein said base portion includes a first end,
wherein an axis of said auxiliary wheel of said auxiliary swivel caster assembly is substantially parallel to the first end, when said locking member engages said locking member receiving portion in a locked position, and
wherein said auxiliary wheel is rotated about its axis to the predetermined position.

13. The cart according to claim 10, wherein said base portion includes a first side end and an opposing second side end, and wherein said auxiliary swivel caster assembly is disposed closer to said first side end than to said second side end.

14. The cart according to claim 10, wherein said auxiliary swivel caster assembly further includes a horn disposed about said auxiliary wheel of said auxiliary swivel caster assembly, wherein said horn includes a notch formed therein as the locking member receiving portion, and wherein said locking member engages the notch, when said tension spring is compressed and said bracket pivots about the generally vertical axis and toward said auxiliary swivel caster assembly.

15. The cart according to claim 10, further comprising a storage structure disposed above said base portion.

16. The cart according to claim 12, wherein said first end is substantially perpendicular to a longitudinal axis of said base portion.

17. The cart according to claim 10, wherein said locking member is enabled to rotate about a vertical axis.

18. A cart comprising:
a base portion;
at least three swivel casters supporting said base portion, each of the at least three swivel casters including a rotatable wheel;
an auxiliary support member connected to said base portion;
an auxiliary swivel caster assembly supporting said base portion, said auxiliary swivel caster assembly including:
a rotatable auxiliary wheel, and
a locking member receiving portion,
wherein said auxiliary wheel is swivelable about a substantially vertically extending axis;
a mounting plate connected to said auxiliary support member;
a locking mechanism pivotably coupled to said mounting plate, said locking mechanism including:
a bracket comprising a locking member; and
a tension spring disposed between said bracket and said auxiliary support member so as to bias said bracket about a generally vertical axis and away from said auxiliary support member,
wherein said locking member selectively engages and disengages said locking member receiving portion, and
wherein, to engage said locking member receiving portion, said bracket pivots about the generally vertical axis and toward said auxiliary swivel caster assembly such that said locking member engages said locking member receiving portion when said auxiliary wheel of said auxiliary swivel caster assembly swivels to a predetermined position.

19. The cart according to claim 18, further comprising:
a comparison spring connected to said base portion and said auxiliary support member, and arranged such that said auxiliary support member is biased away from said base portion and said auxiliary wheel is urged toward a floor supporting said cart.

* * * * *